(12) United States Patent
Broderick et al.

(10) Patent No.: US 10,709,495 B2
(45) Date of Patent: Jul. 14, 2020

(54) DUAL STEP BAILOUT FOR MOTORIZED RF DEVICE

(71) Applicant: Ethicon Endo-Surgery, LLC, Guaynabo, PR (US)

(72) Inventors: Megan A. Broderick, Cincinnati, OH (US); Catherine A. Corbett, Cincinnati, OH (US); Kevin M. Fiebig, Cincinnati, OH (US); Eric N. Johnson, Maineville, OH (US); Richard L. Leimbach, Cincinnati, OH (US); David M. Locke, Springboro, OH (US); Gavin M. Monson, Oxford, OH (US); Rudolph H. Nobis, Mason, OH (US); Mark D. Overmyer, Cincinnati, OH (US); Brett E. Swensgard, West Chester, OH (US); Gregory A. Trees, Cincinnati, OH (US); Aaron C. Voegele, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 1273 days.

(21) Appl. No.: 14/940,424

(22) Filed: Nov. 13, 2015

(65) Prior Publication Data

US 2017/0135747 A1 May 18, 2017

(51) Int. Cl.
*A61B 18/14* (2006.01)
*A61B 17/32* (2006.01)
(Continued)

(52) U.S. Cl.
CPC .... *A61B 18/1445* (2013.01); *A61B 17/00234* (2013.01); *A61B 17/320016* (2013.01);
(Continued)

(58) Field of Classification Search
CPC .... A61B 17/320016; A61B 17/320092; A61B 18/1445; A61B 2017/00398; A61B 2017/00407; A61B 2017/0042; A61B 2017/00477; A61B 2017/00734; A61B 2018/1455; A61B 2090/08021; A61B 2018/00607; A61B 17/32; A61B 17/285;
(Continued)

(56) References Cited

U.S. PATENT DOCUMENTS

2009/0202387 A1   8/2009  Dlugos, Jr. et al.
2010/0089970 A1*  4/2010  Smith .............. A61B 17/07207
                                                                  227/175.1

* cited by examiner

*Primary Examiner* — Ryan J. Severson
*Assistant Examiner* — Socrates L Boutsikaris
(74) *Attorney, Agent, or Firm* — Mintz Levin Cohn Ferris Glovsky and Popeo, P.C.

(57) ABSTRACT

Methods and devices are provided for retracting a cutting assembly in the event of a failure on a motorized electrosurgical device. A surgical device is provided that includes a handle portion with an elongate shaft extending distally therefrom. The elongate shaft has first and second jaws at a distal end, and the jaws are configured to engage tissue. The surgical device also has a cutting assembly configured to cut tissue engaged between the first and second jaws. A drive shaft extends from the handle of the surgical device through the elongate shaft and is coupled to the cutting assembly for moving the cutting assembly. The surgical device has a motorized gear assembly with at least one motor driven gear that is configured to move the drive shaft. The surgical device also has a bailout assembly that is configured to manually move the drive shaft.

15 Claims, 9 Drawing Sheets

(51) Int. Cl.
*A61B 17/00* (2006.01)
*A61B 90/00* (2016.01)
*A61B 17/072* (2006.01)

(52) U.S. Cl.
CPC .............. *A61B 17/07207* (2013.01); *A61B 2017/00017* (2013.01); *A61B 2017/00367* (2013.01); *A61B 2017/00393* (2013.01); *A61B 2017/00398* (2013.01); *A61B 2017/00407* (2013.01); *A61B 2017/00477* (2013.01); *A61B 2017/00734* (2013.01); *A61B 2017/07285* (2013.01); *A61B 2017/320094* (2017.08); *A61B 2018/1455* (2013.01); *A61B 2090/08021* (2016.02)

(58) Field of Classification Search
CPC . A61B 17/29; A61B 17/295; A61B 17/32002; A61B 2017/320028; A61B 2017/320073; A61B 2017/00353; A61B 2017/320093; A61B 2017/320098; A61B 2017/320094; A61F 9/00763
USPC ................................ 606/170, 171, 173, 177
See application file for complete search history.

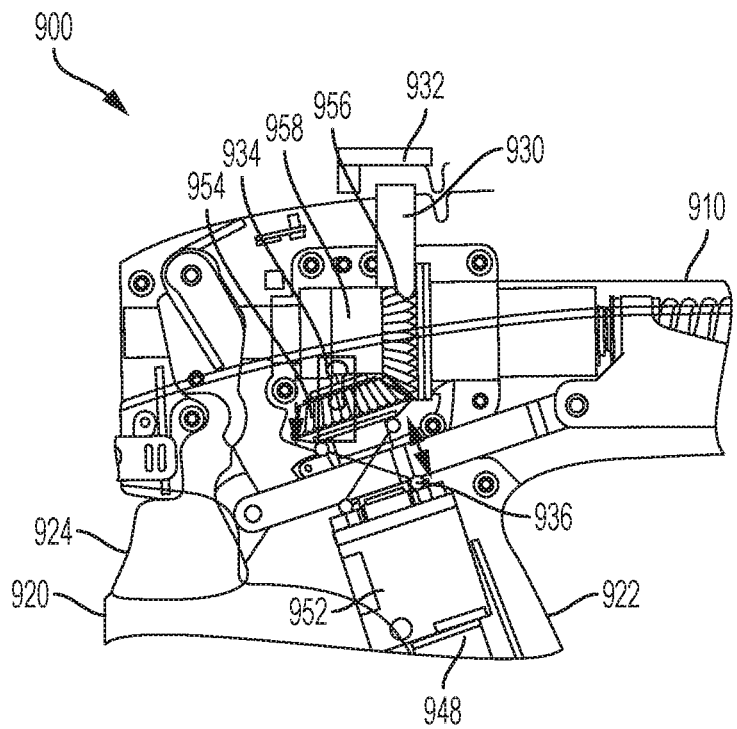
FIG. 15
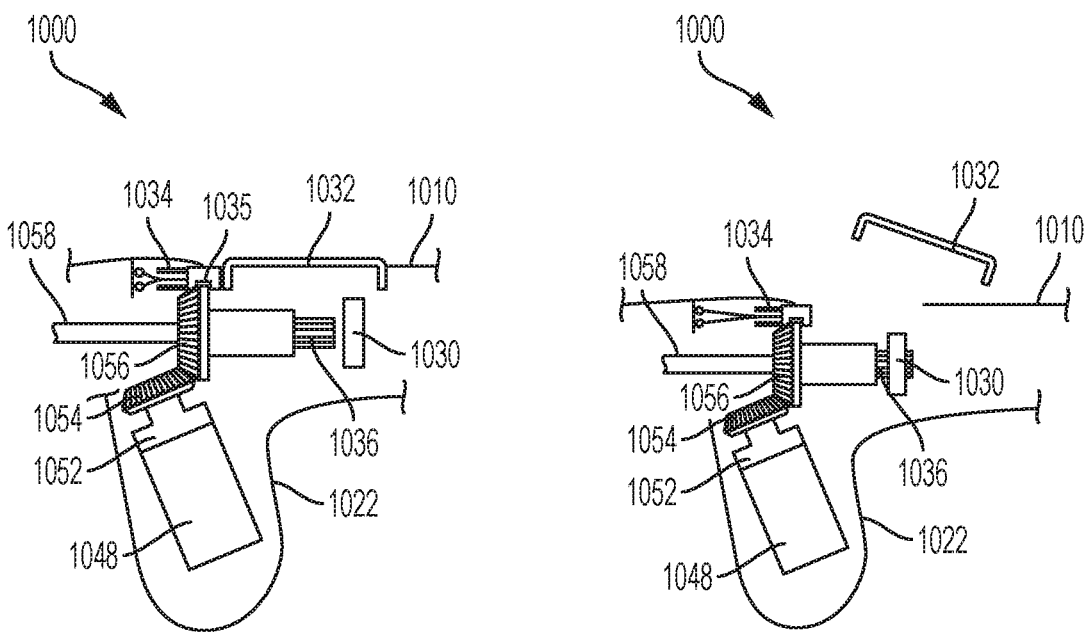
FIG. 16
FIG. 17

DUAL STEP BAILOUT FOR MOTORIZED RF DEVICE

FIELD

Methods and devices are provided for retracting a cutting assembly in the event of a failure on a motorized electrosurgical device.

BACKGROUND

Endoscopic surgical instruments are often preferred over traditional open surgical devices since a smaller incision associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, stapler, clip applier, access device, drug/gene therapy delivery device, and energy device using ultrasound, RF, laser, etc.).

Endoscopic devices are passed through an access port, such as a trocar, to allow the distal end effector to engage tissue within a body cavity of a patient. With powered devices, any problems that occur may prevent removal of the device through the access port. For example, in the event the end effector becomes jammed during a firing stroke or the device otherwise fails, the end effector cannot be removed because tissue is engaged between the jaws. The surgeon may be forced to open up the patient and cut the instrument out of the patient, potentially causing serious harm to the patient.

Accordingly, methods and devices are needed to allow for removal of an instrument even upon failure of the instrument, especially retraction of any mechanisms that prevent the jaws of an end effector from opening and releasing clamped tissue.

SUMMARY

Various methods and devices are provided for retracting a cutting assembly in the event of a failure on a motorized electrosurgical device.

In one aspect, a surgical device is provided that includes a handle portion, a cutting assembly, a drive shaft, a motorized gear assembly, and a bailout gear assembly. The handle portion has an elongate shaft extending distally therefrom with first and second jaws at a distal end that are configured to engage tissue therebetween. The cutting assembly is configured to move relative to the first and second jaws so as to cut tissue engaged between the first and second jaws. The drive shaft extends from the handle through the elongate shaft and is coupled to the cutting assembly for moving the cutting assembly relative to the first and second jaws. The motorized gear assembly has at least one motor driven gear configured to move the drive shaft. The bailout gear assembly has at least one gear configured to manually move the drive shaft.

The surgical device can vary in any number of ways. For example, the motorized gear assembly and the bailout gear assembly can be the same assembly. As another example, the motorized gear assembly can be movable between an engaged position in which the at least one gear on the motorized gear assembly is in engagement with the drive shaft, and a disengaged position in which the at least one gear on the motorized gear assembly is spaced apart from the drive shaft. In another example, the motorized gear assembly can be biased to the engaged position. In yet another example, the bailout gear assembly can have a disengaged position, in which the bailout gear assembly is positioned out of engagement with the drive shaft, and an engaged position, in which the bailout gear assembly is positioned in engagement with the drive shaft. In such an example, movement of the bailout gear assembly from the disengaged position to the engaged position can be effective to cause the motorized gear assembly to disengage from the drive shaft.

In one embodiment, the motorized gear assembly can include a bevel gear, a gear box, and a motor. The motor and gear box can be movable between a first position, in which the motor and gear box are coupled to the bevel gear for driving the bevel gear, and a second position, in which the motor and gear box are disengaged from the bevel gear.

In another example, the motorized gear assembly can include a first bevel gear, a second bevel gear, and a motor assembly. The motor assembly and the second bevel gear can be movable between a first position, in which the motor assembly and the second bevel gear are coupled to the first bevel gear for driving the first bevel gear, and a second position, in which the motor assembly and second bevel gear are disengaged from the first bevel gear.

In yet another embodiment, the handle portion can include a removable pin configured to maintain the motor and gear box in the first position. Removal of the pin can allow movement of the motor and gear box from the first position to the second position.

In another aspect, a surgical device is provided that includes a handle assembly, an elongate body, and a motor-driven cutting assembly. The handle assembly includes an actuator, and the elongate body extends distally from the handle and has an end effector on the distal end thereof. The motor-driven cutting assembly is movable through the end effector so as to cut tissue engaged by the end effector and has a first engaged position in which power can be delivered to the motor-driven cutting assembly to cut tissue engaged between the first and second jaws, and a second disengaged position in which the motor-driven cutting assembly is configured to be manually moved.

The surgical device can vary in any number of ways. For example, power may be prevented from being delivered to the motor-driven cutting assembly in the second disengaged position. In another example, the motor-driven cutting assembly can be biased to the first engaged position. In yet another example, the motor-driven cutting assembly can be manually moved by a bailout gear assembly having at least one gear in the second disengaged position. As another example, the bailout gear assembly can be located on the handle assembly.

As another embodiment, the handle assembly can include a removable pin configured to maintain the motor-driven cutting assembly in the first engaged position. Removal of the pin can allow movement of the motor-driven cutting assembly from the first engaged position to the second disengaged position.

Various methods for cutting tissue are also provided. In one embodiment, a method for cutting tissue is provided that includes engaging tissue between first and second jaws on a surgical device. The method also includes actuating an actuator on a handle assembly of the surgical device to cause power to be delivered to a motorized gear assembly such that the motorized gear assembly drives a cutting assembly through the first and second jaws to at least partially cut the tissue engaged between the first and second jaws. The method can also include moving the motorized gear assembly to a disengaged position and manually driving at least one gear of the motorized gear assembly to cause the cutting assembly to move proximally through the first and second jaws.

The method can vary in any number of ways. For example, moving the motorized gear assembly to a disengaged position can include disconnecting the motorized gear assembly from a power source. As another example, moving the motorized gear assembly to a disengaged position can include overcoming a spring bias of a spring that biases the motorized gear assembly to an engaged position. In yet another example, manually driving at least one gear can include manually moving a bailout gear assembly to move at least one gear into engagement with the at least one gear of the motorized gear assembly. In another example, moving the motorized gear assembly to a disengaged position can include removing a pin on the surgical device that maintains the motor-driven cutting assembly in an engaged position.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 15 is a side cutaway view of another embodiment of a powered surgical device;

FIG. 16 is a side cutaway view of another embodiment of a powered surgical device;

FIG. 17 is another side cutaway view of the powered surgical device of FIG. 16;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. To the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for retracting a cutting assembly in the event of a failure on a motorized electrosurgical device. In particular, methods and devices are provided for driving a drive shaft and/or a bevel gear manually on a motorized electrosurgical device.

Figure 1:
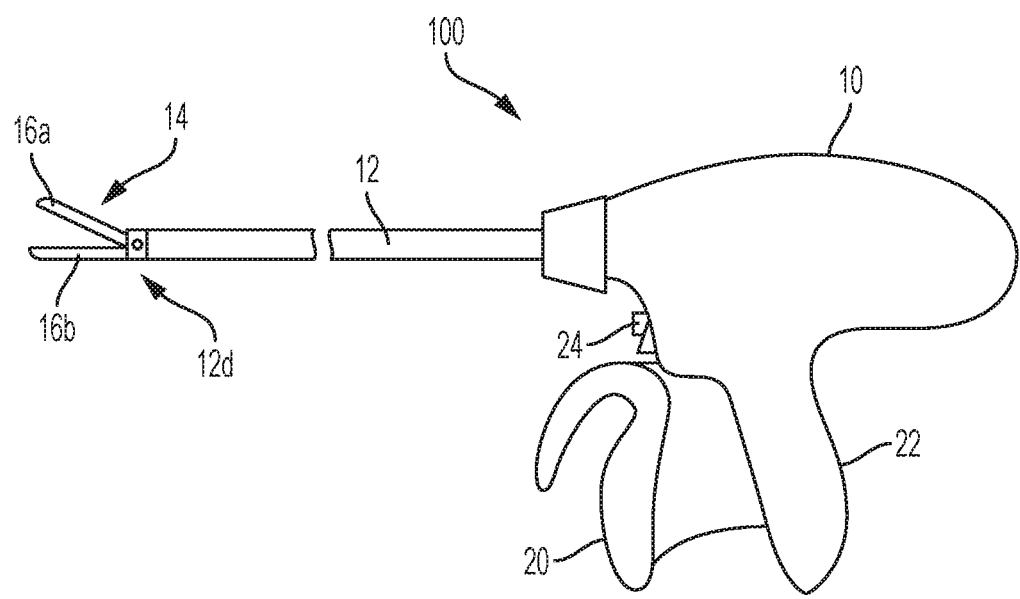
FIG. 1 is a side view illustration of one embodiment of a powered surgical device.

FIG. 1 illustrates one embodiment of a surgical device configured to grasp and cut tissue. As shown, the illustrated surgical device 100 generally includes a proximal handle portion 10, a shaft portion 12, and an end effector 14 for grasping tissue. The proximal handle portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle portion 10 includes a stationary grip 22 and a closure grip 20 that is movable toward and away from the stationary grip 22 to open and close jaws of the end effector 14. The shaft portion 12 extends distally from the proximal handle portion and has a lumen (not shown) extending therethrough for carrying mechanisms for actuating the end effector 14.

The end effector can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can be in direct contact for engaging tissue therebetween. In the illustrated embodiment, the upper jaw 16a pivots relative to the shaft portion 12 and relative to the lower jaw 16b while the lower jaw 16b remains stationary. While the illustrated jaws 16a, 16b have a substantially elongate and straight shape, a person skilled in the art will appreciate that one or both of the jaws 16a, 16b can be in various directions. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset and spaced apart from the stationary grip 22 and the jaws 16a, 16b of the end effector 14 are open. The closure grip 20 can have a second position where it is positioned adjacent to, or substantially in contact with, the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the closure grip 20 can be coupled to gears that interact with a rack disposed within the handle. Manual movement of the closure grip 20 toward the stationary grip 22 can move the rack either proximally or distally relative to the end effector 14 to either pull or push the jaws 16a, 16b closed. In other embodiments, the drive shaft can include or be coupled to a drive screw that can be moved proximally by a drive nut that is rotated by a series of gears. In powered embodiments, a motor can be disposed in the proximal handle portion 10 and manual movement of the closure grip 20 can cause a control signal to be sent to the motor, which can interact with various gears or other components to cause the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

In certain embodiments the surgical device can also have a second actuator, such as actuator 24, that can be separate from the closure actuator 20. The second actuator can be configured to advance a cutting assembly, apply energy to tissue, or both, and is referred to herein as a "firing actuator." The firing actuator 24 can have various sizes, shapes, and configurations, but in the illustrated embodiment it is in the form of a button or trigger that can be depressed by a user. In another embodiment, the firing actuator 24 can be in the form of a switch, lever, etc., that can be slid, pivoted, or otherwise moved by a user. Depressing or pivoting the actuator can activate various elements in the device, and can cause a cutting assembly to advance through the end effector and/or cause energy to be delivered to the jaws. For example, depressing or pivoting the firing actuator can cause a cutting assembly to advance distally and/or retract proximally relative to the jaws 16a, 16b. More specifically, the firing actuator can be in electrical communication with a motor disposed in the proximal handle portion 10. The motor can be operatively coupled to the cutting assembly using known components, such as one or more gears and a rack or drive screw.

Figure 2:
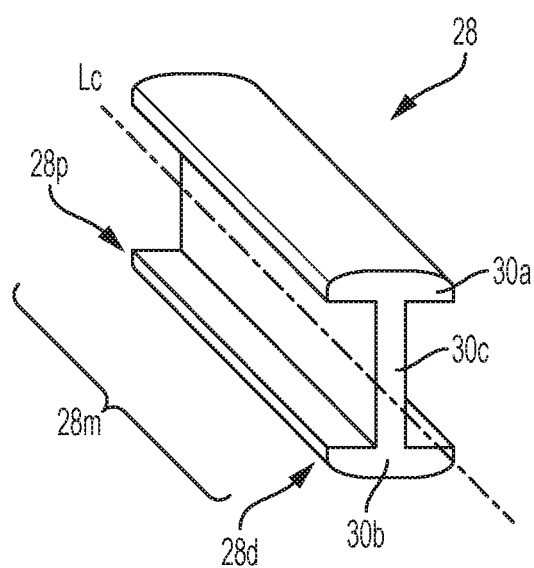
FIG. 2 is a perspective view illustration of a compression member of the powered surgical device of FIG. 1.

The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels through slots formed in each jaw to pull the jaws into a parallel orientation and to compress tissue therebetween. The compression member 28 can include a cutting element (not shown) positioned at the distal end 28d thereof and formed on a connecting portion 30c of the compression member 28. In some embodiments, the cutting element can be integrally formed with the distal end 28d of the compression member 28. The cutting element can have a sharp or serrated edge configured to transect the tissue. In some embodiments, the cutting element can be recessed relative to distal ends of upper and lower flanges 30a, 30b of the I-beam compression member 28 so that compression occurs prior to transecting or cutting of the tissue. In another embodiment, the cutting element can include a shaft having a knife blade that is not attached to a compression member such that the cutting assembly can advance and retract relative to the jaws without applying compression to the tissue.

Figure 3:
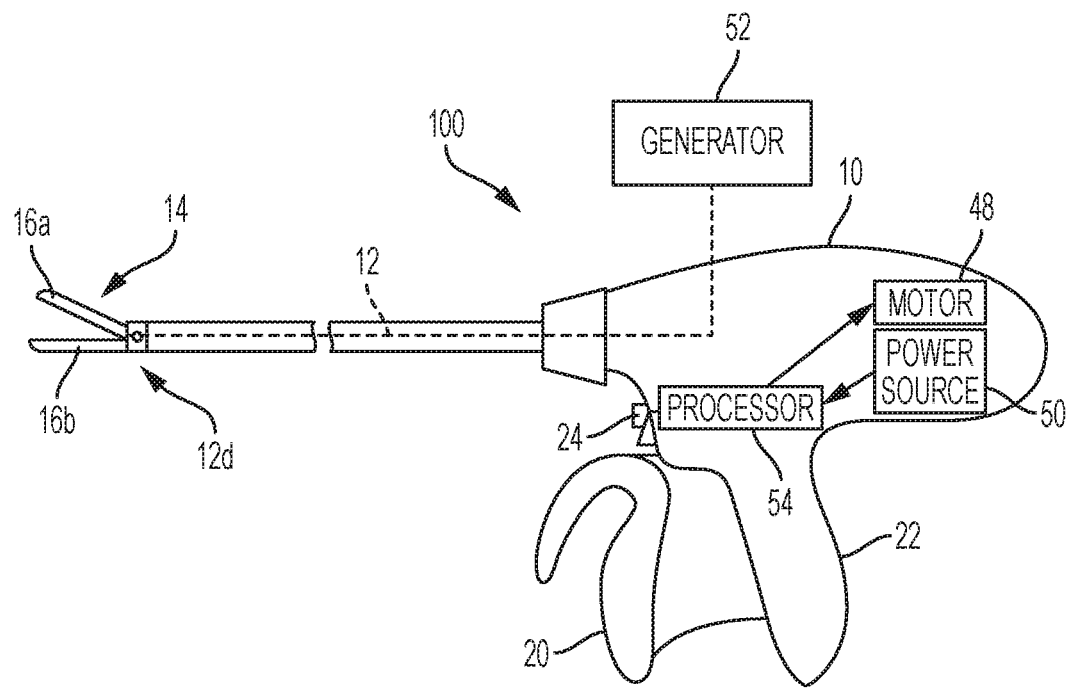
FIG. 3 is a side view illustration of the powered surgical device of FIG. 1.

As shown in FIG. 3, the handle portion 10 of the surgical device 100 can include components for operating the device, such as a motor 48, a power source 50, a generator 52, and a processor 54, as well as various sensors (not shown). The device 100 can also include various components for delivering energy, such as radiofrequency or ultrasound energy, to tissue, and these components can be disposed at various locations in the device 100, such as in the proximal handle portion 10 and/or in the jaws 16a, 16b. The firing actuator 24 can be coupled to the processor 54, and the processor 54 can be coupled to the motor 58, the power source 50, and/or the generator 52 (as well as any sensors provided). Firing the actuator 24 sends a signal to the processor 54, which can cause the power source 50 to provide power to the motor 48 through the processor 54. The motor 48 can drive the cutting assembly, and the processor 54 can control a speed and a direction of the motor, which in turn alters a speed and a direction of the cutting assembly.

The generator 52 can be a separate unit that is electrically connected to the surgical device 100 to decrease the size and weight of the surgical device 100, and it can be operatively coupled to an actuator on the surgical device so that the device is configured to apply energy to tissue engaged by the end effector when the actuator is activated. The generator can be operably coupled to the firing actuator 24 or the generator can be coupled to a second actuator. The generator can be any suitable generator known in the art, such as an RF generator or an ultrasound generator. A lumen (not shown) of the shaft portion 12 can carry electrical leads or wires that can deliver electrical energy to components of the end effector 14. The generator 52 can be coupled to the power source 50, such as a battery disposed in the proximal handle portion 10 or it can be coupled to an external power source, such as an electrical outlet or have its own power source.

Figure 4:
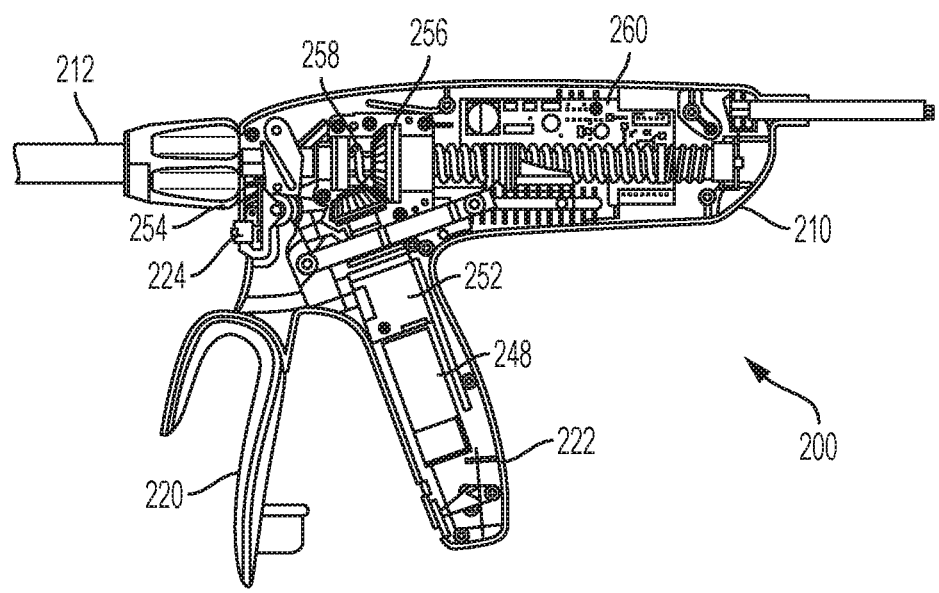
FIG. 4 is a side cutaway view of another embodiment of a powered surgical device.

FIG. 4 illustrates one exemplary configuration of a surgical device 200 having components for operating the device. The surgical device 200 can generally be configured and used similar to the surgical device 100 of FIGS. 1-3. As seen in FIG. 4, the surgical device 200 has a shaft portion 212, and a proximal handle portion 210 including a closure grip 220 and a stationary grip 222. The surgical device 200 has a firing actuator 224 that is configured to advance distally and/or retract proximally a cutting assembly through an end effector (not shown) positioned on a distal end of the shaft portion 212. The firing actuator 224 is a button that can be depressed by a user. The firing actuator 224 is coupled to and in communication with a processor 260, which can include a circuit board and/or a controller. The processor 260 can be in communication with a motor 248, a power source such as a battery, and/or a generator. The motor 248 is disposed in the proximal handle portion 210, and it can be operatively coupled to a gear box 252, which is operably coupled to a motor bevel gear 254. The motor bevel gear 254 is operably coupled in turn to a drive bevel gear 256, which is operably coupled to a drive shaft 258. Activation of the firing actuator 224 can thus provide a signal to the processor 260. The processor 260 can cause power to be delivered from the power source to the motor 248, which rotates the gear box 252. The gear box 252 causes the motor bevel gear 254 to rotate, which engages with and rotates the drive bevel gear 256, which drives the drive shaft 258 distally or proximally. Upon rotation of the drive bevel gear 256, the drive shaft 258 can be driven distally or proximally through known means, such as a thread along the drive shaft 258. Distal movement of the drive shaft 258 advances the cutting assembly distally through an end effector. Proximal movement of the drive shaft 258 retracts the cutting assembly proximally from the end effector. A person skilled in the art will appreciate that the drive shaft can be advanced and retracted using a number of different techniques, such as a rack system, one or more linkages, a ball bearing and nut system, a bevel and spur gear system, etc.

As indicated above, the surgical device 200 has a generator (not shown) that is operatively coupled to an actuator on the surgical device 200 so that the device 200 is configured to apply energy to tissue engaged by the end effector when the actuator is activated. The generator can be operably coupled to the firing actuator 224 or the generator can be coupled to a second actuator. The generator can be any suitable generator known in the art, such as an RF generator or an ultrasound generator. A lumen (not shown) of the shaft portion 212 can carry electrical leads or wires that can deliver electrical energy to components of the end effector.

Under normal operation of a surgical device as described above, power can be supplied from a power source, e.g., the battery, through a processor to a motor, resulting in distal or proximal movement of a cutting assembly through an end effector positioned on a distal end of the surgical device. In particular, the processor instructs the power source to provide power to the motor. In certain instances, the surgical device may fail to successfully complete a cutting stroke, for example if the device jams during cutting because of thick tissue or if a power failure occurs. Removing the surgical device from a patient before retracting the cutting assembly may cause significant harm to the patient, though. If the surgical device malfunctions during a firing stroke, i.e., prior to full advancement and full retraction of the cutting assembly, a surgeon may be required to retract the cutting assembly from the jaws of the end effector. Accordingly, a bailout mechanism is provided that can allow retraction of the cutting assembly in the event of a malfunction.

In general, a surgical device can be provided with a handle and an elongate shaft extending distally therefrom. The elongate shaft can have an end effector at a distal end thereof, which can have first and second jaws. The jaws can be configured to engage tissue therebetween. A cutting assembly can be configured to move relative to the first and second jaws so as to cut tissue engaged between the first and second jaws. A drive shaft can extend from the handle through the elongate shaft. The drive shaft can couple to the cutting assembly and can be configured to move the cutting assembly relative to the first and second jaws. The drive shaft can be moved by a motorized gear assembly with at least one motor driven gear. A bailout gear assembly can be positioned on the handle. The bailout gear assembly can be configured to engage with the drive shaft and/or the gear assembly. The bailout gear assembly can be configured to manually move the drive shaft and/or the motorized gear assembly during a bailout operation. Under a normal operation, the surgical device can be configured to advance and/or retract the cutting assembly from the jaws of the end effector by actuation of a motor. However, the surgical device can also have a bailout operation in which the bailout gear assembly engages the drive shaft and/or the motor gear assembly. The motor and/or motorized gear assembly can be disengaged in some embodiments during the bailout operation. Once the bailout gear assembly has engaged the drive shaft and/or the motorized gear assembly, a surgeon can manually manipulate the bailout gear assembly to drive the drive shaft and/or rotate the motorized gear assembly, to thereby drive the drive shaft. Driving the drive shaft and/or rotating the motorized gear assembly can cause the cutting assembly to move proximally relative to the first and second jaws, retracting the cutting assembly out of the first and second jaws. The first and second jaws can then open to release tissue engaged between, and a surgeon can subsequently withdraw the surgical device from a patient. The bailout operation may allow a surgeon to rapidly remove the surgical device during any emergency situation, for example if normal operation of the device malfunctions, while minimizing any harm to the patient. Manual bailout of the cutting assembly in the form of directly driving the drive shaft and/or rotating the gear assembly to drive the drive shaft may also be fast and less prone to continued device errors than other mechanisms, ensuring a safe retraction during a potentially high-stress situation in which the surgeon is attempting to monitor the patient and safely remove the device at the same time.

Figure 5:
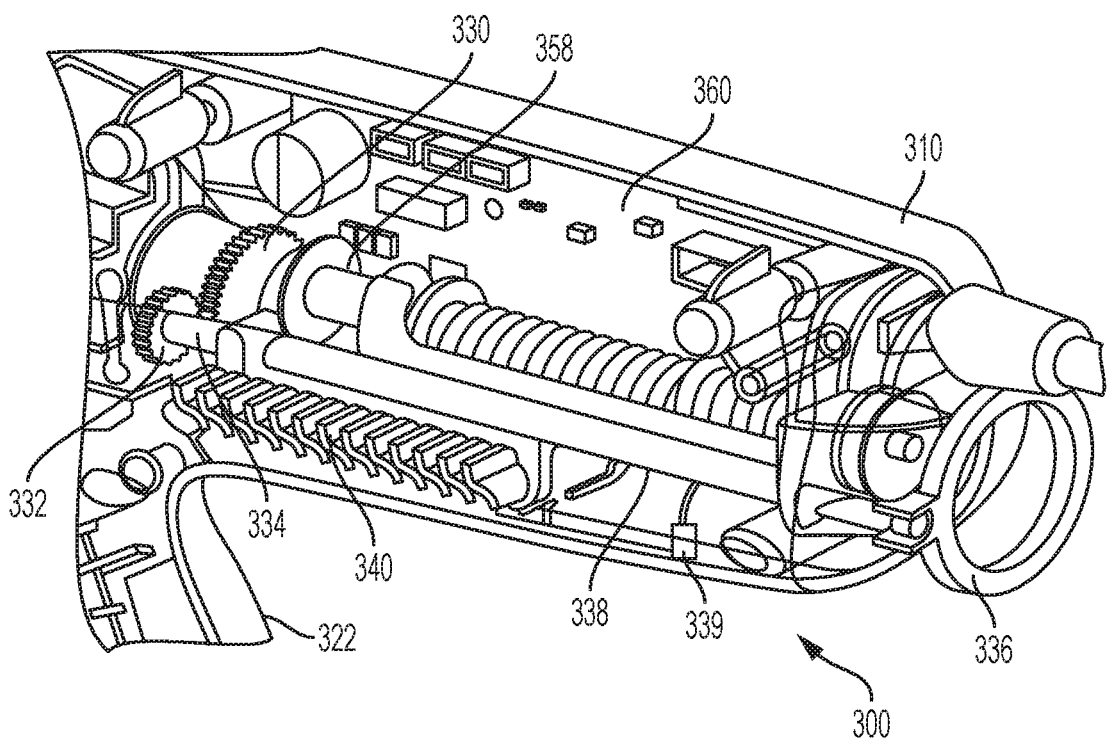
FIG. 5 is a perspective, partially cutaway view of another embodiment of a powered surgical device.

The bailout gear assembly can engage the drive shaft either directly or through a series of gears and be manually rotated to retract the drive shaft and the cutting assembly after a motor has been disconnected or disengaged from the motor gear assembly. FIG. 5 illustrates a proximal portion of one embodiment of a surgical device 300 having a bailout mechanism. The surgical device 300 can generally be configured and used similar to the surgical devices 100, 200 of FIGS. 1-4. Surgical device 300 has a proximal handle portion 310 including a stationary grip 322, only a portion of which is shown. The surgical device 300 has a shaft portion, a closure grip, and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor 360 within the proximal handle portion 310. The processor 360 is in communication with a motor (not shown) and a power source (not shown) such as a battery. The motor is operably coupled to a gear box and is disposed in the proximal handle portion 310. The motor and the gear box are operatively coupled to a motor bevel gear (not shown) that is operably coupled to a drive bevel gear (not shown), which either directly or via one or more additional gears or other components is effective to move a drive shaft 358 proximally or distally upon rotation of the drive bevel gear.

In this embodiment, a first bailout spur gear 330 is coupled to the drive bevel gear and rotates with the drive bevel gear. A ring 336 is positioned externally to the proximal handle portion 310 on a proximal end of the proximal handle portion 310. The ring 336 is coupled to a bailout shaft 338. The bailout shaft 338 extends longitudinally in the direction of the drive shaft 358. On an opposite end of the bailout shaft 338 to the ring 336 is a second bailout spur gear 332. The bailout shaft 338 extends through a stopper 340 and a spring 334. The spring 334 biases the second bailout spur gear 332 distally to maintain the second spur gear 332 out of alignment with the spur gear 330 coupled to the drive bevel gear. A switch 339 is positioned in the proximal end of the proximal handle portion 310 and is coupled to the bailout shaft 338. The switch is connected between the processor and the motor and is configured to open and terminate the connection between the processor and the motor when the bailout shaft 338 moves proximally.

When the device is under a normal operation, the first bailout spur gear 330 is rotated by the drive bevel gear, but the first bailout spur gear 330 will not engage with any other gears. The second bailout spur gear 332 remains unmoved and out of engagement with the first bailout spur gear 330. Actuation of the firing actuator sends a signal to the processor 360, which drives the motor by providing power to the motor from the power source. The motor drives the gear box, which drives the motor bevel gear, which drives the drive bevel gear. The drive bevel gear rotates, causing the drive shaft 358 to advance and retract the cutting assembly. The switch 339 is closed, providing a connection between the processor and the motor so that the processor can power the motor.

If a bailout operation of the cutting assembly is required, the ring 336 can be pulled in a proximal direction, moving the ring 336 and the bailout shaft 338 proximally. When the bailout shaft 338 is moved proximally, the switch 339 is opened, severing the connection between the processor 360 and the motor. The motor thus cannot be accidentally activated while the cutting assembly is being retracted during the bailout operation. The spring 334 compresses as force is applied to overcome the spring bias, and the second bailout spur gear 332 is pulled proximally with the motion of the ring 336 and the bailout shaft 338. The second bailout spur gear 332 is brought into alignment with the first bailout spur gear 330 coupled to the drive bevel gear so that gear teeth on each bailout spur gear 330, 332 mesh together. The ring 336 is rotated, which rotates the second bailout spur gear 332. Rotation of the second bailout spur gear 332 causes rotation of the first bailout spur gear 330. Because the first bailout spur gear 330 is coupled to the drive bevel gear, rotation of the first bailout spur gear 330 causes rotation of the drive bevel gear. Rotation of the drive bevel gear drives the drive shaft 358, and the cutting assembly is retracted from the jaws, allowing the jaws to open.

The ring 336 is held proximally by a user during rotation. In various embodiments, the ring can be held proximally by various mechanisms within the device 300 to make rotation of the ring easier. For example, a groove can be made circumferentially around the bailout shaft, and the bailout shaft can extend through a second ring that can be fixed to an interior surface of the proximal handle portion. As the bailout shaft is pulled proximally during a bailout operation, the second ring can snap into the grove on the bailout shaft and hold the bailout shaft in a proximal position. After a bailout operation, the ring can be forced distally to cause the second ring to disengage from the groove.

The ring 336 is configured to allow rotation in either direction to allow both advancement and retraction of the cutting assembly. Other variations can allow rotation of the ring in only one direction to allow only retraction of the cutting assembly. The cutting assembly can be retracted as long as the ring 336 is rotated. Other embodiments can include mechanisms to prevent over-retraction, such as a stopper positioned in the path of retraction in the proximal handle portion to contact the cutting assembly and prevent further retraction.

The surgical device 300 can be reused and normal operation can be resumed by releasing the ring 336 and allowing the spur gear 332 to move distally out of alignment with the spur gear 330. The switch 339 can be closed as the bailout shaft 338 returns to its original distal position. Other variations can prevent the surgical device from being reused to prevent a malfunctioning surgical device from being used in other operations. For example, a groove can be made circumferentially around the bailout shaft, and the bailout shaft can extend through a second ring that can be fixed to an interior surface of the proximal handle portion. As the bailout shaft is pulled proximally during a bailout operation, the second ring can snap into the grove on the bailout shaft and hold the bailout shaft in a permanently-proximal position. The spur gears thus could not be disengaged. The switch can also be permanently held open when the switch is opened during a bailout operation. The permanently-opened switch would permanently break the connection between the motor and the processor.

Figure 6:
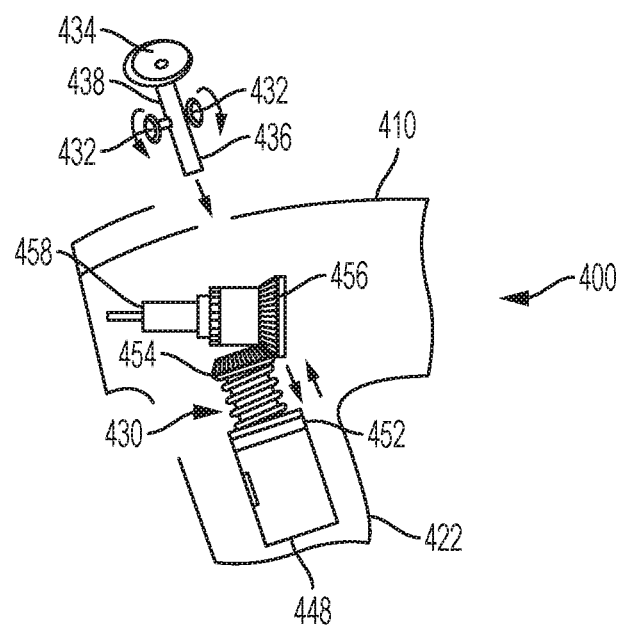
FIG. 6 is a side, cutaway, partially exploded view of another embodiment of a powered surgical device showing a bailout shaft.
Figure 7:
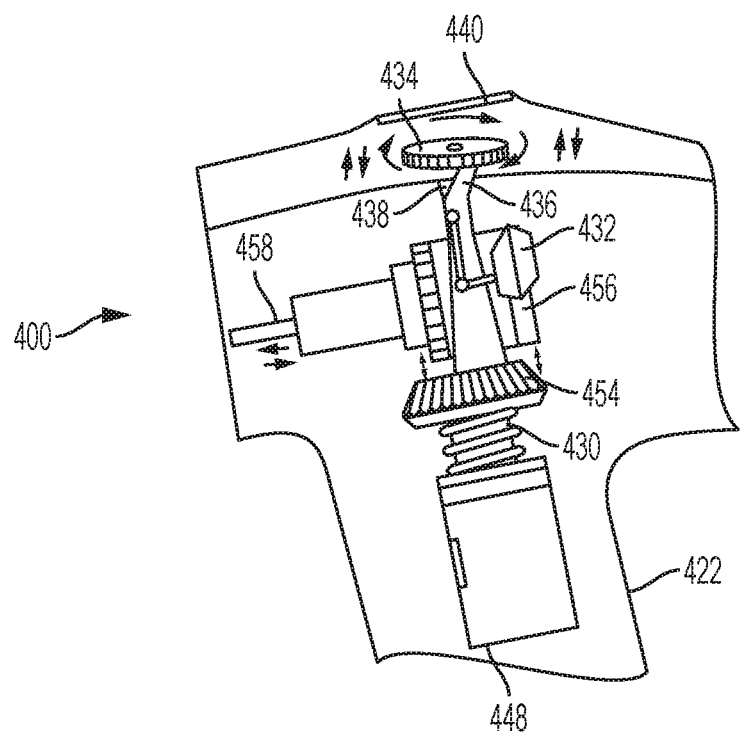
FIG. 7 is a side cutaway view of the powered surgical device of FIG. 6.
Figure 8:
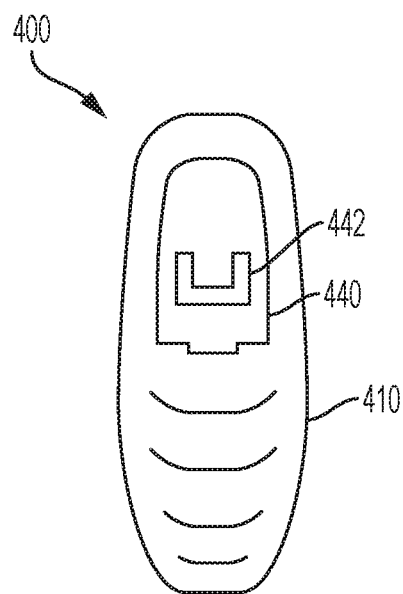
FIG. 8 is a top view of the powered surgical device of FIG. 6.

FIGS. 6-8 illustrate another embodiment of a surgical device 400 having a bailout mechanism. The surgical device 400 can generally be configured and used similar to the surgical devices 100, 200 of FIGS. 1-4. Surgical device 400 has a proximal handle portion 410 including a stationary grip 422. The surgical device 400 has a shaft portion, a closure grip, and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 410. The processor is in communication with a motor 448 and a power source (not shown) such as a battery. The motor 448 is operably coupled to a gear box 452 and is disposed in the proximal handle portion 410. The motor 448 and the gear box 452 are operatively coupled to a motor bevel gear 454 that is operably coupled to a drive bevel gear 456, which either directly or via one or more additional gears or other components is effective to move a drive shaft 458 proximally or distally upon rotation of the drive bevel gear 456.

In this embodiment, the motor 448 and the gear box 452 are coupled to the motor bevel gear 454 through a spring 430. The spring 430 biases the motor bevel gear 454 toward the drive bevel gear 456 to keep the motor bevel gear 454 engaged with the drive bevel gear 456. A bailout shaft 436 extends through a top surface of the proximal handle portion 410, past the drive bevel gear 456, and is positioned adjacent to but spaced apart from the motor bevel gear 454. On either side of the bailout shaft 436 are bailout bevel gears 432 configured to engage the drive bevel gear 456. While the surgical device 400 has two bailout bevel gears 432, other variations can have one or more bevel gears positioned to engage the drive bevel gear. The bailout shaft 436 has a bailout knob 434 positioned on the bailout shaft's external end that is external to the proximal handle portion 410 and that is configured to rotate the bailout bevel gears 432. While the surgical device 400 has a knob, other embodiments can use a variety of mechanisms to cause rotation of the one or more bevel gears, for example a lever, a switch, a dial, etc. The bailout knob 434 is configured to be pressed, causing the bailout shaft 436 to move toward the bevel gears 454, 456.

When the device is under a normal operation, the bailout shaft 436, the bailout bevel gears 432, and the bailout knob 434 do not affect operation of the surgical device 400. The bailout shaft 436 is positioned a distance away from the motor bevel gear 454. The bailout bevel gears 432 are also spaced apart from the drive bevel gear 456 and do not engage the drive bevel gear 456. Actuation of the firing actuator causes the processor to drive the motor 448 by providing power to the motor from the power source. The motor 448 drives the gear box 452, which drives the motor bevel gear 454, which is in engagement with the drive bevel gear 456 due to the spring 430. The drive bevel gear 456 rotates, causing the drive shaft 458 to advance and retract the cutting assembly.

If a bailout operation of the cutting assembly is required, the bailout knob 434 can be pressed, as seen in FIG. 7. The bailout shaft 436 moves toward the motor bevel gear 454 due to force applied to the bailout knob 434, and the bailout bevel gears 432 engage with the drive bevel gear 456. An end of the bailout shaft 436 opposite to the bailout knob 434 contacts the motor bevel gear 454 as the bailout shaft 436 is activated. As the bias of the spring 430 is overcome, the motor bevel gear 454 moves away from and out of engagement with the drive bevel gear 456. Thus the motor 448 and the gear box 452 cannot drive the drive shaft 458 because the bevel gears 454, 456 no longer engage one another, preventing accidental activation of the motor 448. The bailout shaft 436 is kept in its engaged position by a locking barb 438 that latches internally in the proximal handle portion 410 when the bailout shaft 436 is engaged. The bailout knob 434 can be rotated to rotate the bailout bevel gears 432, which engage with and rotate the drive bevel gear 456. Rotation of the drive bevel gear 456 causes retraction or advancement of the drive shaft 458 and this retraction or advancement of the cutting assembly.

The bailout knob 434 can be configured to allow rotation in either direction to allow both advancement and retraction of the cutting element. Other variations can allow rotation of the bailout knob in only one direction to allow only retraction of the cutting assembly. The cutting assembly can be retracted as long as the bailout knob 434 is rotated. Variations can include mechanisms to prevent over-retraction, such as a stopper positioned in the path of retraction in the proximal handle portion to contact the cutting assembly and prevent further retraction.

As seen in FIGS. 7 and 8, in one embodiment the surgical device 400 can include a removable cover 440 that must be removed to access the bailout knob 434, and an engagement pathway 442 on a top surface of the device 400 that requires a select amount of pressure in a particular location to force the bailout shaft 436 into an engaged position, preventing accidental engagement of the bailout shaft 436. However, other embodiments do not require a cover and an engagement pathway.

The surgical device 400 can be reused to return to the normal operation by releasing the locking barb 438 and allowing the spring 430 to force the motor bevel gear 454 to move the bailout shaft 436 away from the motor, causing the motor bevel gear 454 to reengage the drive bevel gear 456 and the bailout bevel gears 432 to disengage from the drive bevel gear 456. The motor 448 and the gear box 452 can then drive the drive shaft 458. Other variations can prevent the surgical device from being reused to prevent a malfunctioning surgical device from being used in other operations. For example, the locking barb 438 can be configured to not be releasable once the locking barb 438 latches internally in the proximal handle portion 410 when the bailout shaft 436 is engaged.

Figure 9:
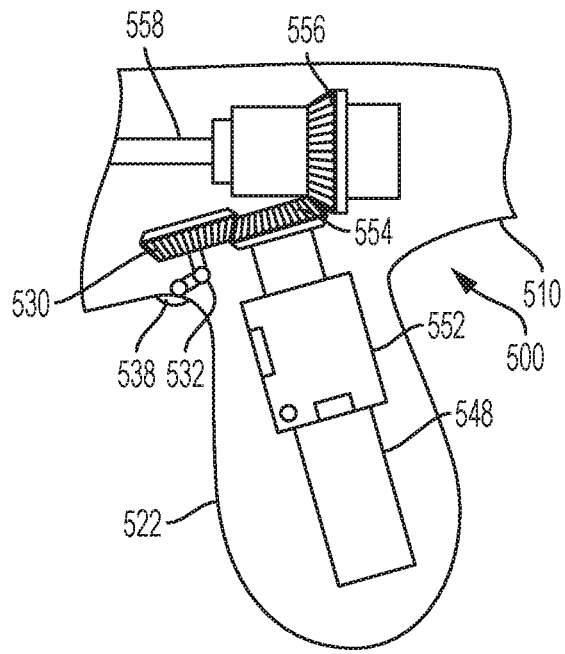
FIG. 9 is a side cutaway view of another embodiment of a powered surgical device.
Figure 10:
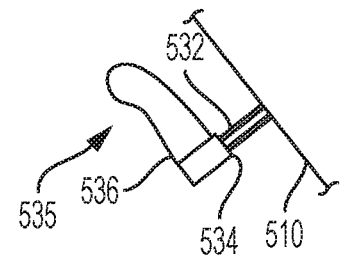
FIG. 10 is a perspective view of part of a bailout mechanism of the powered surgical device of FIG. 9.

FIGS. 9-10 illustrate a proximal portion of another embodiment of a surgical device 500 having a bailout mechanism. The surgical device 500 can generally be configured and used similar to the surgical devices 100, 200 of FIGS. 1-4. Surgical device 500 has a proximal handle portion 510 including a stationary grip 522. The surgical device 500 has a shaft portion, a closure grip, and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 510. The processor is in communication with a motor 548 and a power source (not shown) such as a battery. The motor 548 is operably coupled to a gear box 552 and is disposed in the proximal handle portion 510. The motor 548 and the gear box 552 are operatively coupled to a motor bevel gear 554 that is operably coupled to a drive bevel gear 556, which either directly or via one or more additional gears or other components is effective to move the drive shaft 458 proximally or distally upon rotation of the drive bevel gear 556.

When the device is under a normal operation, a bailout bevel gear 530 operably engages the motor bevel gear 554. A beveled cylinder 532 operably engages the bailout bevel gear 530 and extends from the bailout bevel gear 530 to an external surface of the proximal handle portion 510. The beveled cylinder is configured to be rotatable and to rotate the bailout bevel gear 530. A hook lever 535, illustrated in FIG. 10, has a handle 536 and a beveled cavity 534 that is configured to receive and engage the beveled cylinder 532. The hook lever 535 is stored under a removable cover 538 on the proximal handle portion 510. The cover 538 also covers the beveled cylinder 532. Other variations do not have to have a cover or can cover the hook lever 535 under a first cover and the beveled cylinder under a second cover. The hook lever 535 is configured to be slid onto the beveled cylinder 532 and to be rotatable, which rotates the beveled cylinder 532.

Under normal operations, the bailout bevel gear 530 and the beveled cylinder 532 rotate with rotation of the motor bevel gear 554 and do not affect operation of the surgical device 500. Actuation of the firing actuator sends a signal to the processor, which drives the motor 548 by providing power to the motor 548 from the power source. The motor 548 drives the gear box 552, which drives the motor bevel gear 554, which drives the drive bevel gear 556. The drive bevel gear 556 rotates, causing the drive shaft 558 to advance and retract the cutting assembly.

If a bailout operation of the cutting assembly is required, the hook lever 535 can be pushed onto the beveled cylinder 532 and can be rotated. Rotating the hook lever 535 rotates the beveled cylinder 532, which rotates the bailout bevel gear 530. Because the bailout bevel gear 530 engages with the motor bevel gear 554, the motor bevel gear 554 rotates and in turn rotates the drive bevel gear 556 and ultimately translates the drive shaft 558. Thus rotation of the hook lever 535 causes retraction or advancement of the drive shaft 558 and retraction or advancement of the cutting assembly.

The hook lever 535 is configured to allow rotation in either direction to allow both advancement and retraction of the cutting assembly. Other variations can allow rotation of the hook lever in only one direction to allow only retraction of the cutting assembly. The cutting assembly can be retracted as long as the hook lever 535 is rotated. Other embodiments can include mechanisms to prevent over-retraction, such as a stopper positioned in the path of retraction in the proximal handle portion to contact the cutting assembly and prevent further retraction.

The surgical device 500 can be reused by removing the hook lever 535, returning to the normal operation. The motor 548 and the gear box 552 can then drive the drive shaft 558. Other variations can prevent the surgical device from being reused to prevent a malfunctioning surgical device from being used in other operations. For example, the hook lever 535 can be configured to not be releasable once the hook lever 535 is pushed onto the beveled cylinder 532.

Figure 11:
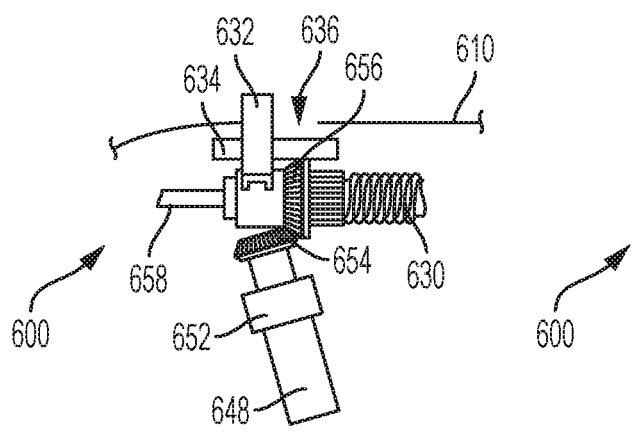
FIG. 11 is a side cutaway view of another embodiment of a powered surgical device.
Figure 12:
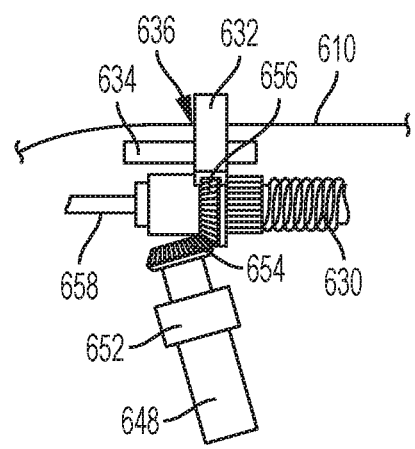
FIG. 12 is another side cutaway view of the powered surgical device of FIG. 11.

FIGS. 11-12 illustrate another embodiment of a surgical device 600 having a bailout mechanism. The surgical device 600 can generally be configured and used similar to the surgical devices 100, 200 of FIGS. 1-4. Surgical device 600 has a proximal handle portion 610. The surgical device 600 has a shaft portion, a closure grip, and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 610. The processor is in communication with a motor 648 and a power source (not shown) such as a battery. The motor 648 is operably coupled to a gear box 652 and is disposed in the proximal handle portion 610. The motor 648 and the gear box 652 are operatively coupled to a motor bevel gear 654 that is operably coupled to a drive bevel gear 656, which either directly or via one or more additional gears or other components is effective to move a drive shaft 658 proximally or distally upon rotation of the drive bevel gear 656.

In this embodiment, a bailout gear 632 is distally and proximally slidably positioned on a bailout shaft 634. The bailout gear 632 extends vertically above the drive shaft 658 and the drive bevel gear 656, and the bailout shaft 634 extends substantially parallel to the drive shaft 658. A portion of the bailout gear 632 passes externally through a slot 636 in a top surface of the proximal handle portion 610 so that the bailout gear 632 is accessible to a user. The bailout gear 632 is configured to slide proximally along the bailout shaft 634 to move into and out of engagement with the drive bevel gear 656. A spring 630 is positioned proximally to the drive bevel gear 656 and biases the drive bevel gear 656 distally to keep the drive bevel gear 656 engaged with the motor bevel gear 654.

When the device is under a normal operation, the bailout gear 632 is positioned distal of the drive bevel gear 656 and does not engage the drive bevel gear 656. Actuation of the firing actuator sends a signal to the processor, which drives the motor 648 by providing power to the motor 648 from the power source. The motor 648 drives the gear box 652, which drives the motor bevel gear 654, which drives the drive bevel gear 656. The drive bevel gear 656 rotates, causing the drive shaft 658 to advance and retract the cutting assembly.

If a bailout operation of the cutting assembly is required, the bailout gear 632 can be slid proximally along the bailout shaft 634 by manually sliding a portion of the bailout gear 632 that extends externally through the slot 636. The bailout gear 632 contacts and engages with the drive bevel gear 656. Further proximal movement overcomes spring bias of the spring 630, causing the drive bevel gear 656 to move proximally to disengage from the motor bevel gear 654. Activation of the motor 648 will thus not cause rotation of the drive bevel gear 656 during the bailout operation. The bailout gear 632 can be rotated manually. Rotating the bailout gear 632 rotates the drive bevel gear 656, which causes translation of the drive shaft 658. Thus rotation of the bailout gear 632 causes retraction or advancement of the drive shaft 658 and retraction or advancement of the cutting assembly.

The bailout gear 632 is held proximally by a user during rotation. In various embodiments, the bailout gear can be held proximally by various mechanisms within the device to make rotation of the bailout gear easier. For example, a tab can extend from the bailout shaft, and the bailout gear can slide over the tab as the bailout gear is moved proximally. The tab can be positioned distally to the bailout gear and keep the bailout gear in a proximal position along the bailout shaft while the bailout gear is rotated. After a bailout operation, the tab can be compressed by a user to allow the bailout gear to slide distally along the bailout shaft.

The bailout gear 632 is configured to allow rotation in either direction to allow both advancement and retraction of the cutting assembly. Other variations can allow rotation of the bailout gear in only one direction to allow only retraction of the cutting assembly. The cutting assembly can be retracted as long as the bailout gear 632 is rotated. Other embodiments can include mechanisms to prevent over-retraction, such as a stopper positioned in the path of retraction in the proximal handle portion to contact the cutting assembly and prevent further retraction.

The surgical device 600 can be reused by moving the bailout gear 632 distally along the bailout shaft 634 to return to the normal operation. The spring 630 will force the drive bevel gear 656 distally, causing the drive bevel gear 656 to reengage the motor bevel gear 654. The motor 648 and the gear box 652 can then drive the drive shaft 658. Other variations can prevent the surgical device from being reused to prevent a malfunctioning surgical device from being used in other operations. For example, the bailout gear 632 can be configured to lock in a proximal position on the bailout shaft once the bailout gear 632 is slid proximally to engage the drive bevel gear 656. Other embodiments can incorporate a cover over the bailout gear and the slot to prevent accidental activation when the bailout gear is not needed and/or a flexible cover that slides with the bailout gear along the slot to prevent any contamination of an interior of the surgical device.

Figure 13:
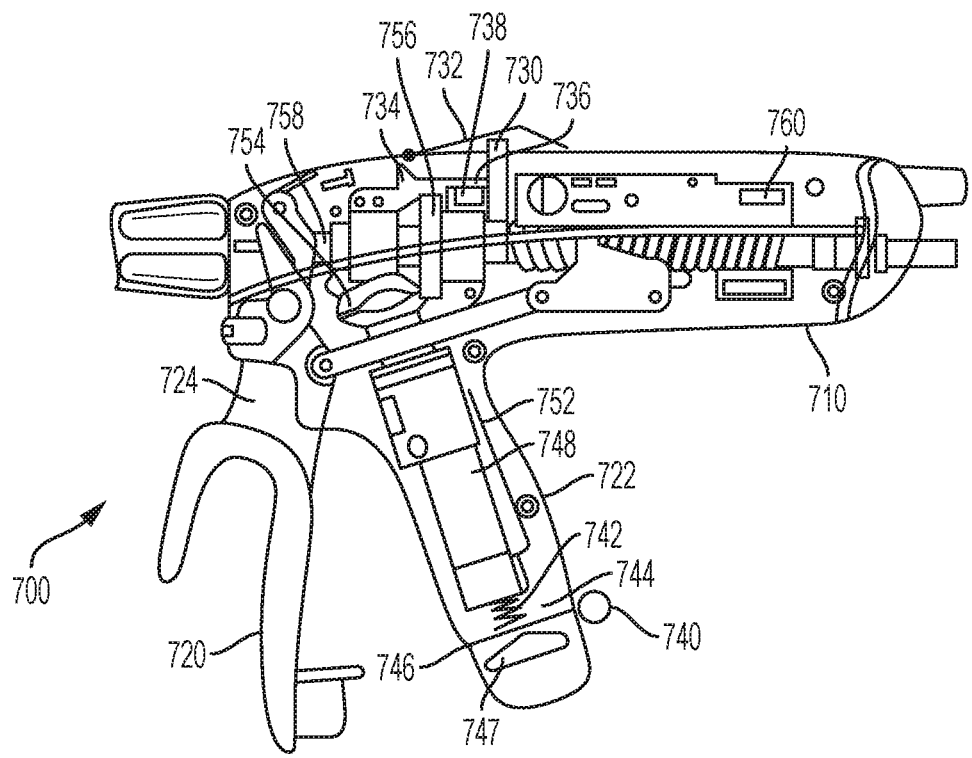
FIG. 13 is a side cutaway view of another embodiment of a powered surgical device.

FIG. 13 illustrates a proximal portion of another embodiment of a surgical device 700 having a bailout mechanism. The surgical device 700 can generally be configured and used similar to the surgical devices 100, 200 of FIGS. 1-4. Surgical device 700 has a proximal handle portion 710 including a stationary grip 722. The surgical device 700 has a shaft portion (not shown), a closure grip 720, and a firing actuator 724 that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor 760 within the proximal handle portion 710. The processor 760 is in communication with a motor 748 and a power source (not shown) such as a battery. The motor 748 is operably coupled to a gear box 752 and is disposed in the proximal handle portion 710. The motor 748 and the gear box 752 are operatively coupled to a motor bevel gear 754 that is operably coupled to a drive bevel gear 756, which either directly or via one or more additional gears or other components is effective to move a drive shaft 758 proximally or distally upon rotation of the drive bevel gear 756.

In this embodiment, a wheel 730 extends vertically above the drive bevel gear 756 and extends externally through the proximal handle portion 710, similar to the prior embodiment. While a wheel is shown in this embodiment, any mechanism capable of rotating a shaft can be used, such as a lever, a dial, a ratchet, etc. The wheel is coupled to a bailout shaft 736, which extends through a shaft support 738 that allows the wheel 730 and the bailout shaft 736 to rotate. A bailout gear 734 is positioned on the end of the bailout shaft 736 opposite to the wheel 730. The bailout gear 734 is operably engaged with the drive bevel gear 756. The wheel 730 is covered by a cover 732 and is configured to rotate the bailout shaft 736 and the bailout gear 734 upon manual rotation of the wheel 730. Because the bailout gear 734 engages the drive bevel gear 756, rotation of the bailout gear 734 rotates the drive bevel gear 756.

A spring 742 is positioned below the motor 748 and the gear box 752 in the stationary grip 722. The spring 742 biases the motor 748 and the gear box 752 into engagement with the motor bevel gear 754. The spring 742 is coupled to a door 744 positioned below the spring 742. The door 744 is pivotally coupled to one side of the stationary grip 722. A grenade pin 740 fixes the door 744 on an opposite side to the pivot side of stationary grip 722, keeping the door 744 in place and the spring 742 applying an upward force on the motor 748 and the gear box 752 to keep the motor 748 and the gear box 752 engaged with the motor bevel gear 754. The grenade pin 740 rests on two support posts 746 in the stationary grip 722. A stop 747 is positioned below the door 744 in the stationary grip 722 and is positioned to interfere with pivoting by the door 744 to prevent the door 744 from over-pivoting.

When the device is under a normal operation, the bailout gear 734, the bailout shaft 736, and the wheel 730 rotate freely with the drive bevel gear 756. Actuation of the firing actuator sends a signal to the processor 760, which drives the motor 748 by providing power to the motor 748 from the power source. The motor 748 drives the gear box 752, which drives the motor bevel gear 754, which drives the drive bevel gear 756. The drive bevel gear 756 rotates, causing the drive shaft 758 to advance and retract the cutting assembly.

If a bailout operation of the cutting assembly is required and normal operations are unavailable, the grenade pin 740 can be pulled free from the stationary grip 722. Removal of the grenade pin 740 allows the door 744 to pivot away from the spring 742, causing the spring 742 to no longer provide an upward force to keep the motor 748 and the gear box 752 engaged with the motor bevel gear 754. The motor 748 and the gear box 752 disengage from the motor bevel gear 754, preventing the motor 748 from accidentally activating and rotating the motor bevel gear 754 during the bailout operation and allowing for an easier manual rotation of the drive bevel gear 756. The cover 732 can be removed, exposing the wheel 730. Manual rotation of the wheel 730 can translate into rotation of the bailout shaft 736, the bailout gear 734, and thus the drive bevel gear 756. Rotation of the drive bevel gear 756 can in turn ultimately drive the drive shaft 758 and retract the cutting assembly.

The wheel 730 is configured to allow rotation in either direction to allow both advancement and retraction of the cutting assembly. Other variations can allow rotation of the wheel in only one direction to allow only retraction of the cutting assembly. The cutting assembly can be retracted as long as the wheel 730 is rotated. Other embodiments can include mechanisms to prevent over-retraction, such as a stopper positioned in the path of retraction in the proximal handle portion to contact the cutting assembly and prevent further retraction.

The surgical device 700 can be reused and returned to the normal operation by releasing the wheel 730 and reinserting the grenade pin 740. The stop 747 can stop the door 744 from over-pivoting, allowing reinsertion of the grenade pin 740 to pivot the door 744 back into the door's original position. The door 744 will thus recompress the spring 742, causing upward force on the motor 748 and the gear box 752, which will reengage the motor bevel gear 754. Other variations can prevent the surgical device from being reused to prevent a malfunctioning surgical device from being used in other operations. For example, the door and the stop can be removed such that pulling the grenade pin causes the motor and the gear box to permanently fall out of engagement with the motor bevel gear. In such an embodiment, the motor and the gear box could be completely removed from the surgical device.

Figure 14:
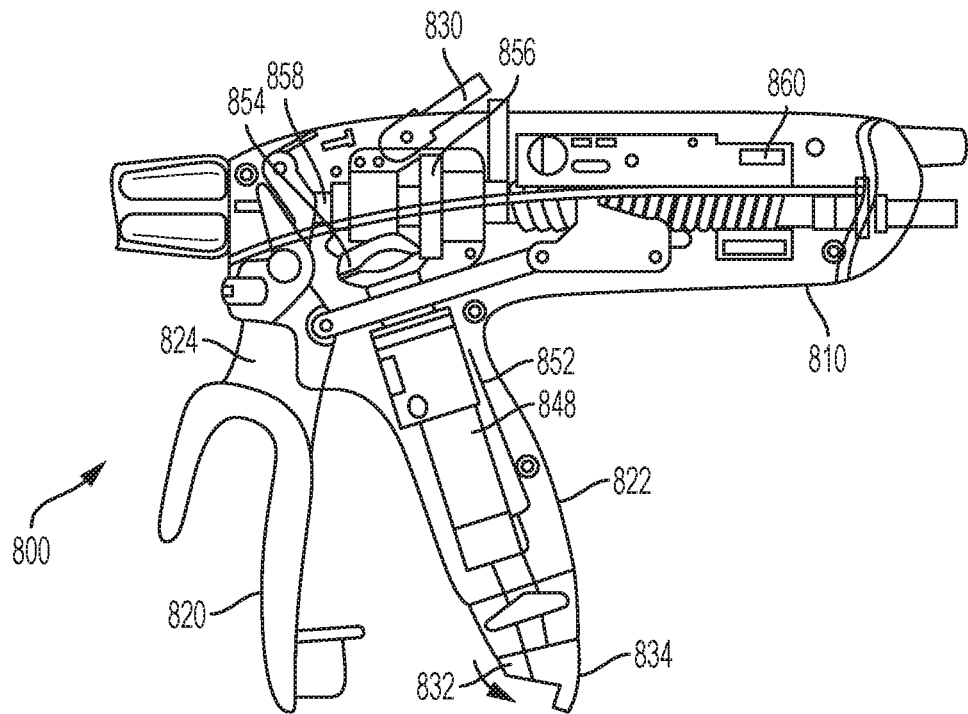
FIG. 14 is a side cutaway view of another embodiment of a powered surgical device.

FIG. 14 illustrates a proximal portion of another embodiment of a surgical device 800 having a bailout mechanism. The surgical device 800 can generally be configured and used similar to the surgical devices 100, 200 of FIGS. 1-4. Surgical device 800 has a proximal handle portion 810 including a stationary grip 822. The surgical device 800 has a shaft portion (not shown), a closure grip 820, and a firing actuator 824 that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor 860 within the proximal handle portion 810. The processor 860 is in communication with a motor 848 and a power source (not shown) such as a battery. The motor 848 is operably coupled to a gear box 852 and is disposed in the proximal handle portion 810. The motor 848 and the gear box 852 are operatively coupled to a motor bevel gear 854 that is operably coupled to a drive bevel gear 856, which either directly or via one or more additional gears or other components is effective to move a drive shaft 858 proximally or distally upon rotation of the drive bevel gear 856.

In this embodiment, a lever 830 extends vertically above the drive bevel gear 856 and extends externally through the proximal handle portion 810. The lever 830 is operably engaged with the drive bevel gear 856 through teeth on the lever 830. The lever 830 is configured to rotate the drive bevel gear 856 upon rotation of the lever 830. While a lever is shown in this embodiment, any mechanism capable of rotating the drive bevel gear can be used, such as a wheel, dial, ratchet, etc. As further shown and similar to the embodiment of FIG. 12, a trap door 834 is positioned below the motor 848 and the gear box 852 in the stationary grip 822. The trap door keeps the motor 848 and the gear box 852 engaged with the motor bevel gear 854. The trap door 834 is pivotally coupled on one side of the stationary grip 822. A stop 832 is positioned below the trap door 834 in the stationary grip 822 and is positioned to interfere with pivoting by the trap door 834 to prevent the trap door 834 from over-pivoting.

When the device is under a normal operation, the lever 830 rotates freely with the drive bevel gear 856. Actuation of the firing actuator sends a signal to the processor 860, which drives the motor 848 by providing power to the motor 848 from the power source. The motor 848 drives the gear box 852, which drives the motor bevel gear 854, which drives the drive bevel gear 856. The drive bevel gear 856 rotates, causing the drive shaft 858 to advance and retract the cutting assembly.

If a bailout operation of the cutting assembly is required, the trap door 834 can be opened. Opening the trap door 834 causes the motor 848 and the gear box 852 to drop away from and disengage from the motor bevel gear 854, preventing accidental activation of the motor 848 during the bailout operation and allowing easier rotation of the drive bevel gear 856. Manual manipulation of the lever 830 can cause rotation of the drive bevel gear 856 and driving of the drive shaft 858, retracting the cutting assembly.

The lever 830 is configured to allow rotation of the drive bevel gear 856 in only one direction to allow only retraction of the cutting assembly. Other variations can allow manipulation of the lever in both directions to allow advancement or retraction of the cutting assembly. The cutting assembly can be retracted as long as the lever 830 is manipulated. Other embodiments can include mechanisms to prevent over-retraction, such as a stopper positioned in the path of retraction in the proximal handle portion to contact the cutting assembly and prevent further retraction.

The surgical device 800 can be reused and returned to normal operation by releasing the lever 830 and closing the trap door 834. The stop 832 can prevent the trap door 834 from over-pivoting, allowing closure of the trap door 834 and upward force on the motor 848 and the gear box 852 to cause re-engagement of the motor bevel gear 854. In another embodiment, a second stop can be added below the motor and the gear box and above the trap door to prevent the motor and the gear box from moving too far away from the motor bevel gear. A tab can be added to a proximal end of the motor to engage the second stop. Other variations can prevent the surgical device from being reused to prevent a malfunctioning surgical device from being used in another operation. For example, the stop can be removed such that opening the trap door causes the motor and the gear box to permanently fall out of engagement with the motor bevel gear. The motor and gear box can be completely removed from the surgical device in some embodiments. In some embodiments, the connection between the motor and the processor can be accomplished through quick connect wires. In these embodiments, a user can quickly and easily disconnect the motor from the processor, which may allow for easier removal of the motor and the gear box from the surgical device and/or prevent activation of the motor and gear box during the bailout operation.

FIG. 15 illustrates a portion of another embodiment of a surgical device 900 having a bailout mechanism. The surgical device 900 can generally be configured and used similar to the surgical devices 100, 200 of FIGS. 1-4. Surgical device 900 has a proximal handle portion 910 including a stationary grip 922. The surgical device 900 has a shaft portion (not shown), a closure grip 920, and a firing actuator 924 that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 910. The processor is in communication with a motor 948 and a power source (not shown) such as a battery. The motor 948 is operably coupled to a gear box 952 and is disposed in the proximal handle portion 910. The motor 948 and the gear box 952 are operatively coupled to a motor bevel gear 954 that is operably coupled to a drive bevel gear 956, which either directly or via one or more additional gears or other components is effective to move a drive shaft 958 proximally or distally upon rotation of the drive bevel gear 956.

In this embodiment, a wheel 930 extends vertically above the drive bevel gear 956 and extends externally through the proximal handle portion 910. The wheel 930 is operably engaged with the drive bevel gear 956 and is covered by a cover 932. The wheel 930 is configured to rotate the drive bevel gear 956 upon manual rotation of the wheel 930. While a wheel is shown in this embodiment, any mechanism capable of rotating the drive bevel gear can be used, such as a lever, dial, ratchet, etc. A ratchet switch 934 is coupled to the motor bevel gear 954 and extends to an external side surface of the proximal handle portion 910. A spring 936 is coupled between the gear box 952 and the motor bevel gear 954. The spring 936 biases the motor bevel gear 954 toward the drive bevel gear 956 to keep the motor bevel gear 954 engaged with the drive bevel gear 956. The ratchet switch 934 is configured to move between two positions. In a first position of the ratchet switch 934, the motor bevel gear 954 is engaged with the drive bevel gear 956 and the spring 936 is in a non-compressed state. The ratchet switch 934 is configured to be moved to a second position by a user, in which the ratchet switch 934 is adjacent the stationary grip 922 and away from the drive bevel gear 956. Because the ratchet switch 934 is coupled to the motor bevel gear 954, movement away from the drive bevel gear 956 causes the motor bevel gear 954 to also move away from the drive bevel gear 956. Movement of the motor bevel gear 954 causes the spring 936 to compress. Once enough force is applied to overcome the spring bias, the spring 936 compresses and the motor bevel gear 954 moves out of engagement with the drive bevel gear 956. On an external side surface of the proximal handle portion 910, the ratchet switch 934 locks into the second position, which keeps the spring 936 compressed and the motor bevel gear 954 out of engagement with the drive bevel gear 956. The ratchet switch 934 is configured to be pushed in to unlock the ratchet switch 934 at each of its two positions.

When the device is under a normal operation, the wheel 930 rotates freely with the drive bevel gear 956. Actuation of the firing actuator sends a signal to the processor, which drives the motor 948 by providing power to the motor 948 from the power source. The motor 948 and the gear box 952 drive the motor bevel gear 954, which drives the drive bevel gear 956. The drive bevel gear 956 rotates, causing the drive shaft 958 to advance and retract the cutting assembly.

If a bailout operation of the cutting assembly is required, the ratchet switch 934 can be moved from its first position to its second position by a user. Moving the ratchet switch 934 to the second position away from the drive bevel gear 956 causes the motor bevel gear 954 to disengage from the drive bevel gear 956 as the spring 936 is compressed, preventing the motor 948 from accidentally activating and rotating the drive bevel gear 956 and allowing for an easier rotation of the drive bevel gear 956. After disengaging the motor bevel gear 954, the cover 932 can be opened by a user, and the wheel 930 can be rotated, causing rotation of the drive bevel gear 956 and driving of the drive shaft 958. As the drive shaft 958 is driven, the cutting assembly retracts.

The wheel 930 is configured to allow rotation of the drive bevel gear 956 in both directions to allow for both advancement and retraction of the cutting assembly. Other variations can allow manipulation of the wheel in only one direction to allow only retraction of the cutting assembly. The cutting assembly can be retracted as long as the wheel 930 is manipulated. Other embodiments can include mechanisms to prevent over-retraction, such as a stopper positioned in the path of retraction in the proximal handle portion to contact the cutting element and prevent further retraction.

The surgical device 900 can be reused and returned to normal operation by releasing the wheel 930 and returning the ratchet switch 934 to its first position. The spring 936 can then apply an upward force on the motor bevel gear 954 to cause re-engagement between the motor bevel gear 954 and the drive bevel gear 956. Other variations can prevent the surgical device from being reused to prevent a malfunctioning surgical device from being used in other operations. For example, the ratchet switch can be configured to only work in one direction to prevent the switch from being returned to its first position such that the motor bevel gear cannot be reengaged with the drive bevel gear.

FIGS. 16-17 illustrate a portion of another embodiment of a surgical device 1000 having a bailout mechanism. The surgical device 1000 can generally be configured and used similar to the surgical devices 100, 200 of FIGS. 1-4. Surgical device 1000 has a proximal handle portion 1010 including a stationary grip 1022. The surgical device 1000 has a shaft portion, a closure grip, and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 1010. The processor is in communication with a motor 1048 and a power source (not shown) such as a battery. The motor 1048 is operably coupled to a gear box 1052 and is disposed in the proximal handle portion 1010. The motor 1048 and the gear box 1052 are operatively coupled to a motor bevel gear 1054 that is operably coupled to a drive bevel gear 1056, which either directly or via one or more additional gears or other components is effective to move a drive shaft 958 proximally or distally upon rotation of the drive bevel gear 956.

In this embodiment, a wheel 1030 is positioned proximally to the drive bevel gear 1056 and is covered by a removable access door 1032. The wheel 1030 has a beveled opening in the wheel's center that is configured to be engageable with a beveled cylinder 1036 coupled to a proximal end of the drive bevel gear 1056. The drive bevel gear 1056 is also coupled to a spring mechanism 1034 that is positioned vertically above the drive bevel gear 1056 such that the drive bevel gear 1056 extends into a slot 1035 on the spring mechanism 1034 but is freely rotatable relative to the spring mechanism 1034. The spring mechanism 1034 contacts the access door 1032 and is in a compressed state when the access door 1034 is closed. The spring mechanism 1034 is configured to expand proximally upon removal of the access door 1032. The drive bevel gear 1056 is configured to move proximally with movement of the spring mechanism 1034, disengaging the drive bevel gear 1056 from the motor bevel gear 1054. The beveled cylinder 1036 on the drive bevel gear 1056 is thus configured to engage the wheel 1030 upon proximal movement of the drive bevel gear 1056 caused by expansion of the spring mechanism 1034 and removal of the access door 1032. The wheel 1030 is configured to be manually rotatable and rotate the drive bevel gear 1056 and the drive shaft 1058.

When the device is under a normal operation, the wheel 1030 does not engage the beveled cylinder 1036 of the drive bevel gear 1056. Actuation of the firing actuator sends a signal to the processor, which drives the motor 1048 by providing power to the motor 1048 from the power source. The motor 1048 drives the gear box 1052, which drives the motor bevel gear 1054, which drives the drive bevel gear 1056. The drive bevel gear 1056 rotates, causing the drive shaft 1058 to advance and retract the cutting assembly.

If a bailout operation of the cutting assembly is required, the access door 1032 can be removed. Removing the access door 1032 allows the spring mechanism 1034 to expand proximally, moving the drive bevel gear 1056 out of engagement with the motor bevel gear 1054, preventing the motor 1048 from accidentally driving the drive shaft 1058 during the bailout operation. The beveled cylinder 1036 on the drive bevel gear 1056 moves into engagement with the wheel 1030. The wheel 1030 can then be rotated to rotate the drive bevel gear 1056 and the drive shaft 1058. As the drive shaft 1058 rotates, the cutting assembly is retracted.

The wheel 1030 is configured to allow rotation of the drive bevel gear 1056 in either direction to allow for both advancement and retraction of the cutting assembly. Other variations can allow manipulation of the wheel in only one direction to allow only retraction of the cutting assembly. The cutting element can be retracted as long as the wheel 1030 is manipulated. Other embodiments can include mechanisms to prevent over-retraction, such as a stopper positioned in the path of retraction in the proximal handle portion to contact the cutting assembly and prevent further retraction.

The surgical device 1000 can be reused and returned to normal operation by releasing the wheel 1030 and replacing the access door 1032, forcing the spring mechanism 1034 to recompress distally and causing the drive bevel gear 1056 to move distally and reengage the motor bevel gear 1054. Other variations can prevent the surgical device from being reused to prevent a malfunctioning surgical device from being used in other operations. For example, the spring mechanism can require such a high force to recompress the spring mechanism that a user will be unable to recompress the spring mechanism and reengage the bevel gears.

Figure 18:
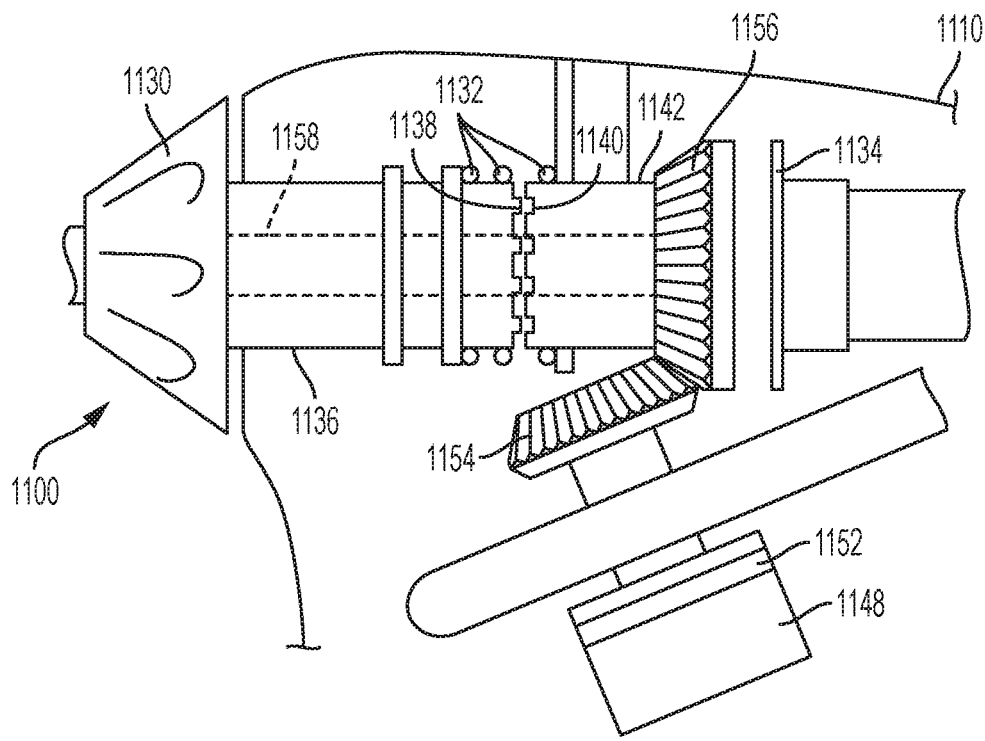
FIG. 18 is a side cutaway view of another embodiment of a powered surgical device.

FIG. 18 illustrates another embodiment of a surgical device 1100 having a bailout mechanism. The surgical device 1100 can generally be configured and used similar to the surgical devices 100, 200 of FIGS. 1-4. Surgical device 1100 has a proximal handle portion 1110. The surgical device 1100 has a shaft portion and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 1110. The processor is in communication with a motor 1148 and a power source (not shown) such as a battery. The motor 1148 is operably coupled to a gear box 1152 and is disposed in the proximal handle portion 1110. The motor 1148 and the gear box 1152 are operatively coupled to a motor bevel gear 1154 that is operably coupled to a drive bevel gear 1156, which either directly or via one or more additional gears or other components is effective to move a drive shaft 1158 proximally or distally upon rotation of the drive bevel gear 1156.

In this embodiment, a first spring 1134 is positioned proximally to the drive bevel gear 1156 and biases the drive bevel gear 1156 distally to engage the motor bevel gear 1154. While a wave spring is shown in the embodiment, any spring can be used. A second spring 1132 is positioned distally from the drive bevel gear 1156 and biases a bailout shaft 1136 distally away from the drive bevel gear 1156. Teeth 1138 are formed on a proximal end of the bailout shaft 1136. Reciprocal teeth 1140 are formed on a distal end of a bevel shaft 1142 that is coupled to the drive bevel gear 1156 on an opposite end of the bevel shaft 1142 to the teeth 1140. On a distal end of the bailout shaft 1136 is positioned a rotation knob 1130 externally from the proximal handle portion 1110. The drive shaft 1158 runs longitudinally within the bailout shaft 1136 and the bevel shaft 1142. The rotation knob 1130 and the bailout shaft 1136 are configured to rotate and to move proximally so that the teeth 1138 can engage the teeth 1140 on the bevel shaft 1142. The bevel shaft 1142 and the drive bevel gear 1156 are configured to rotate and to move proximally to disengage the drive bevel gear 1156 from the motor bevel gear 1154.

When the device is under a normal operation, the rotation knob 1130 and the bailout shaft 1136 do not affect operation of the device 1100 and do not engage the bevel shaft 1142 and the drive bevel gear 1156 because of the spring 1132. The drive bevel gear 1156 engages the motor bevel gear 1154 and rotates, causing the bevel shaft 1142 to rotate freely with the drive bevel gear 1156. Actuation of the firing actuator sends a signal to the processor, which drives the motor 1148 by providing power to the motor 1148 from the power source. The motor 1148 drives the gear box 1152, which drives the motor bevel gear 1154, which drives the drive bevel gear 1156. The drive bevel gear 1156 rotates, causing the drive shaft 1158 to advance and retract the cutting assembly.

If a bailout operation of the cutting assembly is required, the rotation knob 1130 can be moved proximally. Once the spring bias from the spring 1132 is overcome, the rotation knob 1130 can cause the bailout shaft 1136 to move proximally and the teeth 1138 to engage the teeth 1140 on the bevel shaft 1142. Continued application of force proximally on the rotation knob 1130 can cause the bevel shaft 1142 and the drive bevel gear 1156 to overcome the spring bias from spring 1134 and move proximally as well, disengaging the drive bevel gear 1156 from the motor bevel gear 1154 and preventing the motor 1148 from accidentally driving the drive shaft 1158 during the bailout operation. With the teeth 1138, 1140 engaged and the bevel gears 1154, 1156 disengaged, the rotation knob 1130 can be rotated to rotate the drive bevel gear 1156 and the drive shaft 1158. As the drive shaft 1158 rotates, the cutting assembly is retracted.

The rotation knob 1130 is configured to allow rotation of the drive bevel gear 1156 in either direction to allow for both advancement and retraction of the cutting assembly. Other variations can allow rotation of the rotation knob in only one direction to allow only retraction of the cutting assembly. The cutting assembly can be retracted as long as the rotation knob 1130 is rotated. Other embodiments can include mechanisms to prevent over-retraction, such as a stopper positioned in the path of retraction in the proximal handle portion to contact the cutting assembly and prevent further retraction.

The surgical device 1100 can be reused and returned to normal operation by releasing the rotation knob 1130, which causes the springs 1132, 1134 to move the rotation knob 1130, the bailout shaft 1136, the bevel shaft 1142, and the drive bevel gear 1156 distally. The bailout shaft 1136 and the bevel shaft 1142 will disengage while the bevel gears 1154, 1156 will reengage. Other variations can prevent the surgical device from being reused to prevent a malfunctioning surgical device from being used in other operations. For example, the teeth on the bailout shaft and the bevel shaft can permanently engage, preventing the rotation knob and the bailout shaft from disengaging the bevel shaft and the drive bevel gear.

Figure 19:
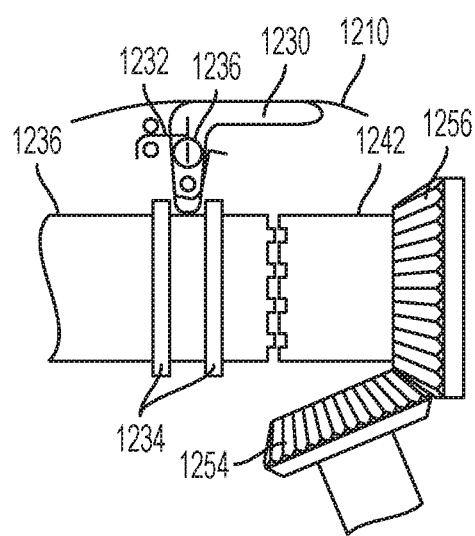
FIG. 19 is a side cutaway view of a bailout mechanism in a powered surgical device.
Figure 20:
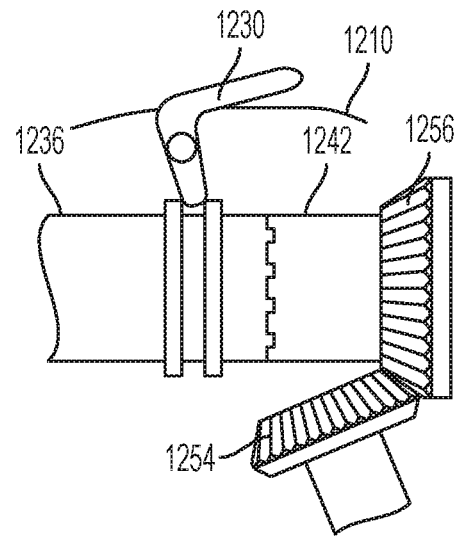
FIG. 20 is another side cutaway view of the bailout mechanism of FIG. 19.

Alternative mechanisms for creating engagement the bailout shaft and the bevel shaft are possible while remaining components of a surgical device are identical to those in FIG. 18. For example as seen in FIGS. 19-20, a lever 1230 can be positioned above a bailout shaft 1236. The lever 1230 can extend externally from the proximal handle portion 1210. The lever 1230 can be biased by a spring 1232, such as a torsion spring, and can engage the bailout shaft 1236 by extending between two stoppers 1234 that extend around the bailout shaft 1236. The spring 1232 can bias the bailout shaft 1236 distally away from a bevel shaft 1242 and a drive bevel gear 1256. Similar to FIG. 18, the bailout shaft 1236 engages the bevel shaft 1242 by proximal movement in which teeth engage one another. Proximal movement is caused by lifting the lever 1230, which rotates about a pivot point 1236. Engagement between the lever 1230 and the bailout shaft 1236 forces the bailout shaft 1236 to move proximally to engage the bevel shaft 1242 coupled to the drive bevel gear 1256. The bevel shaft 1242 and the drive bevel gear 1256 are both forced to move proximally by the movement of the bailout shaft 1236. The drive bevel gear 1256 disengages a motor bevel gear 1254 as the drive bevel gear 1256 moves proximally, as seen in FIG. 20 and similar to FIG. 18. A rotation knob as seen in FIG. 18 would then be used to translate the drive shaft 1236 and retract a cutting assembly.

Figure 21:
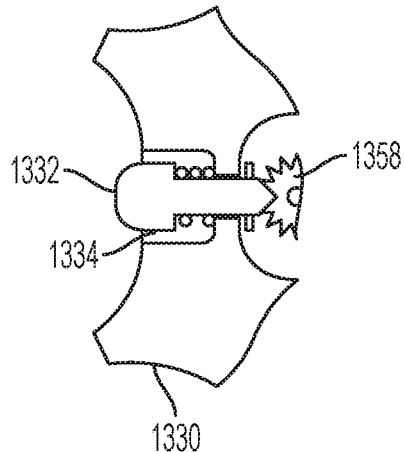
FIG. 21 is a cross sectional view of a rotation knob in a powered surgical device.
Figure 22:
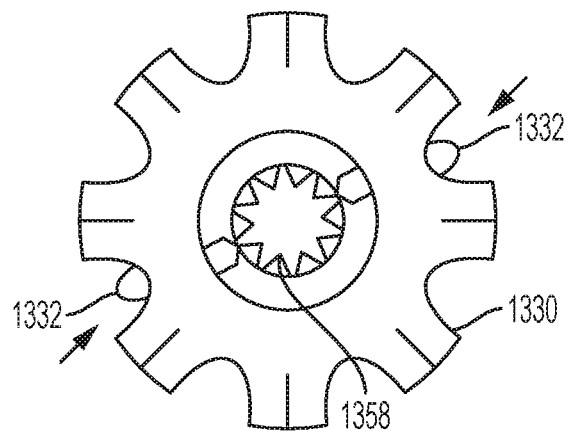
FIG. 22 is an end view of the rotation knob of FIG. 21.

Alternatively, a rotation knob 1330 can engage a drive shaft 1358 directly rather than engaging a bailout shaft with a bevel shaft, as seen in FIGS. 21-22. The rotation knob 1330 has spring plungers 1332 that pass through the rotation knob 1330 and are held radially away from the drive shaft 1358 by springs 1334 to allow free rotation of the drive shaft 1358 under normal operation. Upon depressing the spring plungers 1332 to overcome the spring bias of the springs 1334, the spring plungers 1332 extend radially inward and engage the drive shaft 1358, coupling the rotation knob 1330 to the drive shaft 1358. A drive bevel gear would still need to be disengaged from a motor bevel gear through mechanisms as seen in FIGS. 18-20. The rotation knob 1330 can then be rotated to translate the drive shaft 1358 and retract a cutting assembly, similar to FIG. 18.

Figure 23:
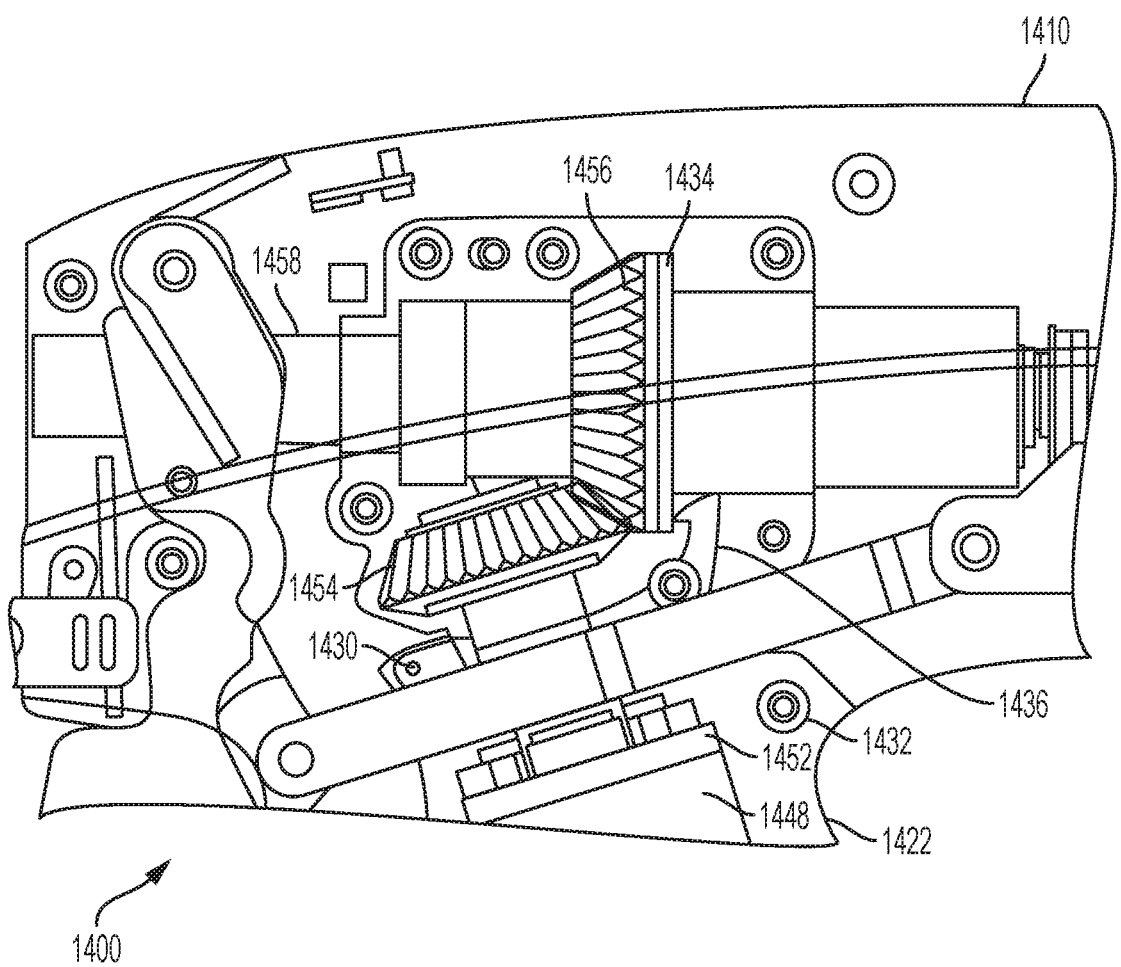
FIG. 23 is a side cutaway view of another embodiment of a powered surgical device.

FIG. 23 illustrates another embodiment of a surgical device 1400 having a bailout mechanism. The surgical device 1400 can generally be configured and used similar to the surgical devices 100, 200 of FIGS. 1-4. Surgical device 1400 has a proximal handle portion 1410 including a stationary grip 1422. The surgical device 1400 has a shaft portion, a closure grip, and a firing actuator (not shown) that can be configured to advance distally and/or retract proximally a cutting assembly through an end effector (not shown) positioned on a distal end of the shaft portion. The closure grip is effective to move jaws of the end effector between open and closed positions. The firing actuator is connected to and in communication with a processor (not shown) within the proximal handle portion 1410. The processor is in communication with a motor 1448 and a power source (not shown) such as a battery. The motor 1448 is operably coupled to a gear box 1452 and is disposed in the proximal handle portion 1410. The motor 1448 and the gear box 1452 are operatively coupled to a motor bevel gear 1454 that is operably coupled to a drive bevel gear 1456, which either directly or via one or more additional gears or other components is effective to move a drive shaft 1458 proximally or distally upon rotation of the drive bevel gear 1456.

In this embodiment, a pin 1430 is inserted into the stationary grip 1422 to couple the stationary grip 1422 to the proximal handle portion 1410 on one side of the stationary grip 1422. On an opposite side of the stationary grip 1422, a pivot point 1432 allows the stationary grip 1422 to pivot in relation to the proximal handle portion 1410. The pin 1430 is configured to be removable, allowing the stationary grip 1422 to disconnect from the proximal handle portion 1410 on a side corresponding to the pin 1430 and to pivot about the pivot point 1432. Pivoting of the stationary handle 1422 is configured to cause the motor bevel gear 1454 to disengage from the drive bevel gear 1456 as the motor bevel gear 1454 pivots with the stationary grip 1422. A pawl 1436 is coupled to the stationary grip 1422 on a side corresponding to the pivot point 1432. The pawl 1436 is configured to engage ratchet features 1434 radially distributed on a proximal side of the drive bevel gear 1456 upon pivot of the stationary grip 1422. The pawl 1436 is configured to cause rotation of the drive bevel gear 1456 due to repeated interaction between the pawl 1436 and the ratchet features 1434 as the stationary grip 1422 is pivoted back and forth on the pivot point 1432.

When the device is under a normal operation, the pin 1430 maintains a connection between the stationary grip 1422 and the proximal handle portion 1410. The pawl 1436 does not move, and the ratchet features rotate with the drive bevel gear 1456. Actuation of the firing actuator sends a signal to the processor, which drives the motor 1448 by providing power to the motor 1448 from the power source. The motor 1448 drives the gear box 1452, which drives the motor bevel gear 1454, which drives the drive bevel gear 1456. The drive bevel gear 1456 rotates, causing the drive shaft 1458 to advance and retract the cutting assembly.

If a bailout operation of the cutting assembly is required, the pin 1430 can be pulled free from the stationary grip 1422. Removal of the pin 1430 can cause the stationary grip 1422 to pivot away from the proximal handle portion 1410 around pivot point 1432, causing the motor bevel gear 1454 and the drive bevel gear 1456 to disengage from one another, preventing the motor 1448 from accidentally activating and translating the drive shaft 1458 during the bailout operation. The pawl 1436 engages the ratchet features 1434 and rotates the drive bevel gear 1456 upon repeated back and forth pivoting of the stationary grip 1422. Rotation of the drive bevel gear 1456 can in turn drive the drive shaft 1458 and retraction of the cutting assembly.

The pawl 1432 is configured to allow rotation of the drive bevel gear 1456 in only one direction to allow only retraction of the cutting assembly. Other variations can allow rotation of the drive bevel gear in either direction to allow advancement and retraction of the cutting assembly. The cutting assembly can be retracted as long as the pawl 1432 and the stationary grip 1422 are pivoted. Other embodiments can include mechanisms to prevent over-retraction, such as a stopper positioned in the path of retraction in the proximal handle portion to contact the cutting assembly and prevent further retraction.

The surgical device 1400 can be reused and returned to the normal operation by pivoting the stationary grip 1422 back into its starting position and replacing the pin 1430, at which position the motor bevel gear 1454 will reengage the drive bevel gear 1456. Other variations can prevent the surgical device from being reused to prevent a malfunctioning surgical device from being used in other operations. For example, the pin can be irreplaceable once removed, causing the motor bevel gear to permanently fall out of engagement with the drive bevel gear.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a handle portion having an elongate shaft extending distally therefrom, the elongate shaft having first and second jaws at a distal end thereof, the jaws being configured to engage tissue therebetween;
a cutting assembly configured to move relative to the first and second jaws so as to cut tissue engaged between the first and second jaws;
a drive shaft extending from the handle portion through the elongate shaft and being coupled to the cutting assembly for moving the cutting assembly relative to the first and second jaws;
a motor driven bevel gear configured to move the drive shaft; and
a bailout bevel gear configured to manually move the drive shaft;
a motor assembly;
wherein the motor assembly and the motor driven bevel gear are movable between a first position, in which the motor assembly and the motor driven bevel gear are coupled to the bailout bevel gear for driving the bailout bevel gear, and a second position, in which the motor assembly and the motor driven bevel gear are disengaged from the bailout bevel gear; and
wherein the bailout bevel gear is configured to assist the motor driven bevel gear to move the drive shaft when the motor driven bevel gear is driven by the motor assembly, and the bailout bevel gear is configured to disengage from the motor driven bevel gear when the bailout bevel gear manually moves the drive shaft.

2. The device of claim 1, wherein the motor driven bevel gear is biased to the first position.

3. The device of claim 1, wherein movement of the bailout bevel gear from engagement with to disengagement from the motor driven bevel gear is effective to cause the motor driven bevel gear to disengage from the drive shaft.

4. The device of claim 1, wherein the motor assembly includes a motor and a gear box configured to drive the motor driven bevel gear, the handle portion includes a removable pin configured to maintain the motor driven bevel gear, the motor, and the gear box in engagement with the drive shaft such that removal of the pin is configured to cause movement of the motor driven bevel gear, the motor, and the gear box away from and out of engagement with the drive shaft.

5. A surgical device, comprising:
a handle assembly including an actuator, a proximal housing portion, and a handle grip;
an elongate body extending distally from the handle assembly and having an end effector on a distal end thereof, the end effector having first and second jaws configured to grasp tissue therebetween;
a motor-driven cutting assembly movable through the end effector so as to cut tissue engaged by the end effector, the motor-driven cutting assembly having a first engaged position in which power can be delivered to the motor-driven cutting assembly to cut tissue engaged between the first and second jaws, and a second disengaged position in which the motor-driven cutting assembly is configured to be manually moved by pivoting the handle grip relative to the proximal housing portion of the handle assembly; and
a motor bevel gear disposed in the handle grip and a bailout bevel gear disposed in the proximal housing portion.

6. The surgical device of claim 5, wherein the motor-driven cutting assembly is biased to the first engaged position.

7. The surgical device of claim 5, wherein the motor-driven cutting assembly is manually moved in the second disengaged position by the bailout bevel gear.

8. The surgical device of claim 5, wherein the handle assembly includes a removable pin configured to maintain the motor-driven cutting assembly in the first engaged position, removal of the pin allowing movement of the motor-driven cutting assembly from the first engaged position to the second disengaged position.

9. The surgical device of claim 8, wherein removal of the pin is configured to allow manual pivoting movement between the handle grip and the proximal housing portion of the handle assembly.

10. The surgical device of claim 5, wherein the motor-driven cutting assembly is configured to move from the first engaged position to the second disengaged position upon movement of the handle grip away from the proximal housing portion.

11. The surgical device of claim 5, wherein motor-driven motion is prevented from being delivered to the motor-driven cutting assembly in the second disengaged position.

12. The surgical device of claim 5, wherein the motor bevel gear and the bailout bevel gear are configured to provide motor-driven actuation to the motor-driven cutting assembly in the first engaged position, and the motor bevel gear is configured to disengage from the motor-driven cutting assembly in the second disengaged position.

13. A surgical device, comprising:
a handle assembly including an actuator, a proximal housing portion, and a handle grip;
an elongate body extending distally from the handle assembly and having an end effector on a distal end thereof, the end effector having a cutting assembly configured to cut tissue engaged by the end effector;
a drive shaft extending from the handle assembly through the elongate body and being coupled to the cutting assembly for moving the cutting assembly through the end effector;
a motor-driven gear disposed in the handle grip and configured to be driven by a motor assembly;
a bailout gear disposed in the proximal housing portion; and
a removable and replaceable pin in the handle assembly;
wherein the surgical device has a first operational mode in which the motor-driven gear and the bailout gear are in engagement with the drive shaft and are configured to cause motor-driven motion of the drive shaft, a second bailout mode in which the motor-driven gear is configured to move relative to and out of engagement with the drive shaft and the bailout gear is configured to be manually driven to cause manually-driven motion of the drive shaft, and the motor-driven gear is configured to move proximally out of engagement with the drive shaft in the second bailout mode upon removal of the pin from the handle assembly.

14. The surgical device of claim 13, wherein the motor-driven gear is configured to move from the second bailout mode to the first operational mode upon replacement of the pin in the handle assembly.

15. The surgical device of claim 13, further comprising a pawl coupled to the handle grip, ratchet features formed on the bailout gear, and a pivot coupled to the handle grip and the proximal housing portion such that the handle grip is configured to pivot relative to the proximal housing portion in the second bailout mode, wherein pivoting of the handle grip relative to the proximal housing portion is configured to cause the pawl to engage with the ratchet features and drive the bailout gear in the second bailout mode.

* * * * *